US011401234B2

(12) United States Patent
Ogrodzinski et al.

(10) Patent No.: US 11,401,234 B2
(45) Date of Patent: Aug. 2, 2022

(54) DEUTERATED COMPOUNDS AND USES THEREOF

(71) Applicant: Biostatus Limited, Shepshed (GB)

(72) Inventors: Stefan Ogrodzinski, Shepshed (GB); Paul Smith, Shepshed (GB); Stephanie McKeown, Shepshed (GB); Laurence Patterson, Shepshed (GB); Rachel Jane Errington, Shepshed (GB)

(73) Assignee: ONCOTHERICS VENTURES LIMITED, Shepshed (GB)

(*) Notice: Subject to any disclaimer, the term of this patent is extended or adjusted under 35 U.S.C. 154(b) by 0 days.

(21) Appl. No.: 16/543,790

(22) Filed: Aug. 19, 2019

(65) Prior Publication Data
US 2020/0270200 A1 Aug. 27, 2020

Related U.S. Application Data

(63) Continuation of application No. 14/420,184, filed as application No. PCT/BG2013/052106 on Aug. 7, 2013, now Pat. No. 10,385,009.

(30) Foreign Application Priority Data

Aug. 8, 2012 (GB) ..................................... 1214169

(51) Int. Cl.
| C07C 225/36 | (2006.01) |
| C07B 59/00 | (2006.01) |
| C07C 291/04 | (2006.01) |
| A61K 31/136 | (2006.01) |
| A61K 31/277 | (2006.01) |
| A61K 45/06 | (2006.01) |
| G01N 31/22 | (2006.01) |

(52) U.S. Cl.
CPC .......... *C07C 225/36* (2013.01); *A61K 31/136* (2013.01); *A61K 31/277* (2013.01); *A61K 45/06* (2013.01); *C07B 59/001* (2013.01); *C07C 291/04* (2013.01); *G01N 31/225* (2013.01); *C07B 2200/05* (2013.01); *C07C 2603/24* (2017.05)

(58) Field of Classification Search
CPC . C07C 225/36; C07C 291/04; C07C 2603/24; C07B 59/001; C07B 2200/05
See application file for complete search history.

(56) References Cited

U.S. PATENT DOCUMENTS

| 4,197,249 | A | 4/1980 | Murdock et al. |
| 5,132,327 | A | 7/1992 | Patterson |
| 6,376,531 | B1 | 4/2002 | Bell |
| 6,603,008 | B1 | 8/2003 | Anda et al. |
| 2009/0156807 | A1 | 6/2009 | Ishmael |

FOREIGN PATENT DOCUMENTS

| JP | H04502166 | 4/1992 |
| JP | 2006501140 | 1/2006 |
| WO | 1995026325 | 10/1995 |
| WO | WO9526325 | * 10/1995 |
| WO | WO9965992 | * 12/1999 |
| WO | 2006031719 | 3/2006 |
| WO | 2006096458 | 9/2006 |
| WO | 2011124927 | 10/2011 |

OTHER PUBLICATIONS

Patterson; et al., "AQ4N: a new approach to hypoxia-activated cancer chemotherapy," British Journal of Cancer, vol. 83, Issue 12, Dec. 5, 2000, pp. 1589-1593.
Timmins, "Deuterated drugs; updates and obviousness analysis," Expert Opinion on Therapeutic Patents, htttps://www.tandfonline.com/loi/ietp20, vol. 27, Issue 12, Sep. 14, 2017, 10 pages.
Database Registry (STN) RN 118997 4-82-0, entered STN on Oct. 25, 2009, 1 page.
Benghiat; et al., "Phase 1 dose escalation study of AQ4N, a selective hypoxic cell cytotoxin, with fractionated radiotherapy (RT): First report," Journal of Clinical Oncology, vol. 22, No. 14, Jul. 2004,1 page.
Benghiat; et al., "The use of pharmacokinetic and pharmacodynamic endpoints to determine dose of AQ4N given with radiotherapy (RT)," Journal of Clinical Oncology, vol. 23, No. 16 suppl., Jun. 2005, 2 pages.
McKeown, "Defining normoxia, physoxia and hypoxia in tumours—implications for treatment response," British Institute of Radiology, Jan. 2014, pp. 1-12.

(Continued)

*Primary Examiner* — Barbara P Badio
(74) *Attorney, Agent, or Firm* — Leber IP Law; Shelly M. Fujikawa

(57) ABSTRACT

An anthraquinone compound of formula I (such as the compounds of formulae II to X) and processes for making the same are provided. Pharmaceutical compositions for use in the treatment of cancer, optionally in combination with an agent capable of reducing the level of oxygenation of a tumour, are also provided. Additionally, an option for combination with chemotherapeutic and radiotherapeutic modalities to enhance overall tumour cell kill is provided. Methods for the detection of cellular hypoxia, both in vivo and in vitro, are additionally provided.

Formula I

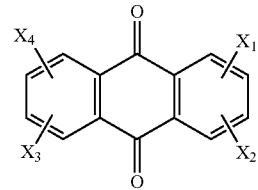

41 Claims, 20 Drawing Sheets

(56) References Cited

OTHER PUBLICATIONS

Nesbitt; et al., "Targeting Hypoxic Prostate Tumors Using the Novel Hypoxia-Activated Prodrug OCT1002 Inhibits Expression of Genes Associated with Malignant Progression," Clinical Cancer Research, Oct. 3, 2016, pp. 1797-1808.
Dyck; et al., "Effects of Deuterium Substitution on the Catabolism of beta-Phenylethylamine: An In Vivo Study," Journal of Neurochemistry, vol. 46, Issue 2, Feb. 1986, pp. 399-404.
Abertella; et al., "Hypoxia-Selective Targeting by the Bioreductive Prodrug AQ4N in Patients with Solid Tumors: Results of a Phase I Study," Clinical Cancer Research, vol. 14, Feb. 15, 2008, pp. 1096-1104.
Hones; et al., "Can we detect an effect of OCT-1002 or AQ4N on hypoxic cells in pancreatic ductal adenocarconima (PDA) tissue in vivo in KPC mice by immunohistochemical analysis of DNA damage by measuring ?H2AX?," Cambridge Research Institute, UK, unpublished, 2 pages.
Steward; et al., "The use of pharmacokinetic and pharmacodynamic end points to determine the dose of AQ4N, a novel hypoxic cell cytoxin, given with fractionated radiotherapy in a phase I study," Annals of Oncology, vol. 18, Apr. 17, 2017, pp. 1098-1103.
King, "Deuterization: Is It Enough To Get 5- or 7-Year Exclusivity for A 505(8)(2) Product?," Camargo Pharmaceutical Services, Aug. 2, 2017, 10 pages.
Phillips, "Targeting the hypoxic fraction of tumours using hypoxia-activated prodrugs," Cancer Chemother Pharmacol, Jan. 25, 2016, pp. 441-457.
Papadopoulos; et al., "A Phase 1 Open-Label, Accelerated Dose-Escalation Study of the Hypoxia-Activated Prodrug AQ4N in Patients with Advanced Malignancies," Clinical Cancer Research, vol. 14, Issue 21, Nov. 1, 2008, pp. 7110-7115.
Martin, "Hansch analysis 50 years on," Opinion, vol. 2, May/Jun. 2012, pp. 435-442.
Loadman; et al., "A Preclinical Pharmacokinetic Study of the Bioreductive Drug AQ4N," The American Society for Pharmacology and Experimental Therapeutics, vol. 29, No. 4 (1), Apr. 2001, pp. 422-426.
Smith; et al., "Flow Cytometric Analysis and Confocal Imaging of Anticancer Alkylaminoanthraquinones and Their N-Oxides in Intact Human Cells Using 647-nm Krypton Laser Excitation," Cytometry, vol. 27, Jan. 1997, pp. 43-53.
Siegel; et al., "Hydrogen-Deuterium Exchange Studies Utilizing a Thermospray Mass Spectrometer Interface," Analytical Chemistry, vol. 60, Oct. 1, 1988, pp. 2090-2095.
Benghiat; et al., "Phase 1 dose escalation study of AQ4N, a selective hypoxic cell cytotoxin, with fractionated radiotherapy (RT): First report," Journal of Clinical Oncology, vol. 22, No. 14 suppl, Jul. 2004, pp. 2091.
Benghiat; et al., "The use of pharmacokinetic and pharmacodynamic endpoints to determine dose of AQ4N given with radiotherapy (RT)," Journal of Clinical Oncology, vol. 23, No. 16 suppl, Jun. 2005, pp. 2062.
Chemical datasheet for 1, 4-dihydroxy-5,8-bis[2-{( 1,1,2,2-tetradeulerio-2-hydroxyethyl)amino }elhylamino] anthracene-9, 10-dione, Oct. 25, 2009.
Milosevic, M.; et al., "Androgen Withdrawal in Patients Reduces Prostate Cancer Hypoxia: Implications for Disease Progression and Radiation Response," Cancer Research 2007, vol. 67: (13), Jul. 1, 2007, pp. 6022-6025.
Milosevic, M.; et al., "Tumor Hypoxia Predicts Biochemical Failure following Radiotherapy for Clinically Localized Prostate Cancer," Clinical Cancer Research, vol. 18(7), Apr. 1, 2012, pp. 2108-2114.
Ming, L.; et al., "Androgen deprivation results in time-dependent hypoxia in LNCaP prostate tumours: Informed scheduling of the bioreductive drug AQ4N improves treatment response," International Journal of Cancer, vol. 132, 2013, pp. 1323-1332.
Nesbitt, H.; et al., "Targeting Hupoxic Prostate Tumors Using the Novel Hypoxia-Activated Prodrug OCT1002 Inhibits Expression of Genes Associated with Malignant Progression," Clinical Cancer Research, Apr. 2017, 12 pages.

Chouaib, S.; et al., "Hypoxic stress: obstacles and opportunities for innovative immunotherapy of cancer," Oncogene, vol. 36, Jan. 26, 2017, pp. 439-445.
Albertella, Mark R.; et al., "Hypoxia-Selective Targeting by the Bioreductive Prodrug AQ4N in Patients with Solid Tumors: Results of a Phase I Study," Clin Cancer Research, vol. 14, Feb. 2008, pp. 1096-1104.
Benito, Juliana; et al., "Targeting hypoxia in the leukemia microenvironment," Int J Hematol Oneal., vol. 2(4), Aug. 1, 2013, pp. 279-288.
Bennewith, Kevin L.; et al., "Targeting hypoxic tumour cells to overcome metastasis," BMC Cancer, vol. 11:504, Nov. 30, 2011, pp. 1-6.
Brizel, David M.; et al., "Tumor Oxygenation Predicts for the Likelihood of Distant Metastases in Human Soft Tissue Sarcoma," Cancer Research, vol. 56, Mar. 1, 1996, pp. 941-943.
Chang, Joan; et al., "Hypoxia-Mediated Metastasis, Tumor Microenvironment and Cellular Stress," Advances in Experimental Medicine and Biology, Chapter 3, 2014, pp. 55-81.
Fox, Mary E.; et al., :Long-Term Inhibition of DNA Synthesis and the Persistence of Trapped Topoisomerase II Complexes in Determining the Toxicity of the Antitumor DNA Intercalators mAMSA and Mitoxantrone, Cancer Research, vol. 50, Sep. 15, 1990, pp. 5813-5818.
Fyles, A.; et al., "Tumor Hypoxia Has Independent Predictor Impact Only in Patients With Node-Negative Cervix Cancer," Journal of Clinical Oncology, vol. 20, No. 3, Feb. 1, 2002, pp. 680-687.
Lalani, Alshad S.; et al., "Selective Tumor Targeting by the Hypoxia-Activated Prodrug AQ4N Blocks Tumor Growth and Metastasis in Preclinical Models of Pancreatic Cancer," Clinical Cancer Research, vol. 13(7), 2007, pp. 2216-2225.
Margolin, Adam A., "Oncogenic Driver Mutations: Neither Tissue-Specific nor Independent," Science Translational Medicine, vol. 5, Issue 214, Dec. 4, 2013, 214 pages.
Kandoth, Cyriac; et al., "Mutational landscape and significance across 12 major cancer types," Nature, vol. 502 (7471), Oct. 17, 2013, pp. 333-339.
McAllister, Sandra S.; et al., "The tumour-induced systemic environment as a critical regulator of cancer progression and metastasis," Nature Cell Biology, vol. 16, No. 8, Aug. 2014, pp. 717-727.
McKeown, S R, "Defining normoxia, physoxia and hypoxia in tumours—implications for treatment response," Br J Radial, Jan. 2014, pp. 1-12.
Patterson, Laurence H.; et al., "Antitumour prodrug development using cytochrome P450 {CYP) mediated activation," Anti-Cancer Drug Design, vol. 14, Dec. 1999, pp. 473-486.
Pitson, Graham; et al., "Tumor Size and Oxygenation are Independent Predictors of Nodal Disease in Patients with Cervix Cancer," Int. J. Radiation Oncology Biol. Phys., vol. 51, No. 3, Nov. 1, 2001, pp. 699-703.
Rankin, Erinn B.; et al., "Hypoxic control of metastasis," Science, vol. 352(6282), Apr. 8, 2016, pp. 175-180.
Carnero, Amancio; et al., "The hypoxic microenvironment: A determinant of cancer stem cell evolution," Bioessays, vol. 38, Oct. 2015, pp. S65-S74.
Kushner; et al.,"Pharmacological uses and perspectives of heavy water and deuterated compounds," Canadian Journal of Physiology and Pharmacology, vol. 77(2), 1999, pp. 79-88.
Dyck; et al., "Effects of deuterium substitution on the catabolism of beta-phenylethylamine: An in vivo study," Journal of Neurochemistry, vol. 46(2), 1986, pp. 399-404.
Foster, "Deuterium isotope effects in studies of drug metabolism," Trends in Pharmacological Sciences, vol. 5(12), 1984, pp. 524-527.
A complete copy of: Siegel M. M.: "Hydrogen-Deuterium Exchange Studies Utilizing a Thermospray Mass Spectrometer Interface", Analytical Chemistry, American Chemical Society, US, vol. 60, No. 19, Jan. 1, 1998 (Jan. 1, 1998), pp. 2090-2095, XP001157215, ISSN: 0003-2700, DOI: 10.1021/AC00170A021 the whole document.
Siegel M. M.: "Hydrogen-Deuterium Exchange Studies Utilizing a Thermospray Mass Spectrometer Interface", Analytical Chemistry, American Chemical Society, US, vol. 60, No. 19, Jan. 1, 1998 (Jan. 1, 1998), pp. 2090-2095, XP001157215, ISSN: 0003-2700, DOI: 10.1021/AC00170A021 the whole document.

(56) References Cited

OTHER PUBLICATIONS

Tayar; et al., "The lipophilicity of deuterium atoms. A comparison of shake-flask and HPLC methods", International Journal of Pharmaceutics, vol. 19 (1984), pp. 271-281.
Wade, "Deuterium isotope effects on noncovalent interactions between molecules", Chemico-Biological Interactions 117, (1999) pp. 191-217.

* cited by examiner

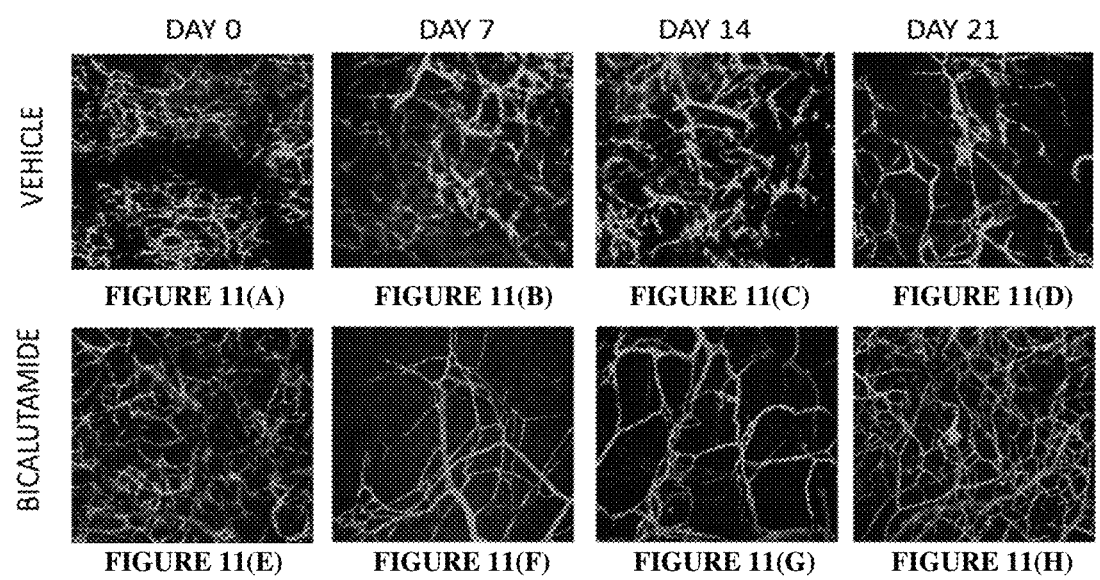

Vehicle + OCT1002 (day 7)

Bicalutamide + OCT1002 (day 7)

DEUTERATED COMPOUNDS AND USES THEREOF

CROSS REFERENCE TO RELATED APPLICATION

This application is a continuation of U.S. patent application Ser. No. 14/420,184, filed Feb. 6, 2016, which is a National Stage Entry of International Patent Application No. PCT/GB2013/052106, filed Aug. 7, 2013, which claims priority from Great Britain Patent Application No. 1214169.3, filed Aug. 8, 2012, the entire disclosures of which are incorporated herein by reference.

TECHNICAL FIELD

The present invention relates to novel anthraquinone compounds and uses of the same, for example in the treatment of cancer.

BACKGROUND

The therapeutic advantage of an anticancer drug depends primarily on the extent to which the agent shows selective activity for tumour cells and the limiting toxicity towards non-target tissues. Frequently the poor quality of the vasculature within the growing tumour mass compromises the delivery of drugs, nutrients and oxygen. It is recognised that tumours can have significantly lower median oxygen levels (approximately 1% oxygen; pO2 7.5 mmHg) compared to normal tissues (~5.5% oxygen; 42 mmHg) (summarised from data presented by Brown and Wilson, 2004). In addition, oxygenation levels can vary throughout the tumour due to intermittent opening and closing of tumour blood vessels; poor vascularisation, especially in the tumour core, contributes to oxygen levels often being below 0.1% oxygen (1 mm Hg). Tumour cells experiencing varying degrees of hypoxia, relative to normally perfused tissues, can compromise treatment effectiveness and contribute to the malignancy. Hypoxia-selective agents (e.g. bioreductive drugs) comprise one class of agents that can be used to target tumour cells in very low oxygen environments by virtue of a selective activation to a cytotoxic form under reduced oxygenation, addressing the problems of non-target tissue toxicity, hypoxic cell drug resistance and cancer progression.

Poor oxygenation results in a relative state of hypoxia when compared with normoxic conditions in which oxygenation has not been compromised. Poor oxygenation within tumours can modify the responses to treatment modalities and contribute to cancer progression. Cells in such hypoxic areas are particularly resistant to treatment with many of the conventionally used anticancer drugs; this is attributed to poor drug delivery and/or lack of intrinsic tumour cell sensitivity of viable but quiescent cells. Radiotherapy is also less effective at very low oxygen levels since the cytotoxicity of ionising radiation is enhanced by the presence of oxygen (Radiobiology For The Radiologist, Hall E J, Giaccia A J, Lippincott Williams & Wilkins, (2005)). Recent evidence shows that tumour cells can adapt to low oxygen conditions and change the pharmacodynamic responses to anticancer agents through the induction of active cellular protective mechanisms (Vaupel and Mayer 2007, *Cancer Metastasis Rev* 26(2): 225-239). Additionally, it is recognized that tumour cells that survive hypoxic stress often show a more malignant metastatic phenotype (Vaupel P, Metabolic microenvironment of tumor cells: a key factor in malignant progression, Exp Oncol 2010; 32, 125-127); this has significant consequences for the patient. Following treatment with modalities that target predominantly the better-oxygenated cells, the stress-resistant hypoxic cells often repopulate the tumour with cells that have an enhanced potential to spread to distant tissues. The development of more malignant metastatic tumours is often the precursor to a more significant disease-related morbidity and the death of the patient.

An attractive approach is the use of a hypoxia activated prodrug that is non-toxic towards adequately oxygenated cells found in systemic tissues, but becomes activated or converted to a cytotoxic form under reduced oxygenation conditions. N-oxide derivatives of cytotoxic alkylaminoanthraquinones provide anthraquinone pro-drugs that show almost no cytotoxicity. Importantly these prodrugs are capable of being converted in vivo under the anaerobic/hypoxic conditions found within neoplastic tissue. Specificity for the tumour is ensured since systemic tissues, except for tumours, almost never experience oxygen levels low enough to facilitate the production of the cytotoxic drug.

The anthraquinone N-oxide AQ4N (CAS #136470-65-0) is a prodrug that is selectively bioreduced to AQ4, a potent DNA topoisomerase II inhibitor, in hypoxic tumour cells. Previous publications have taught the fundamental properties and in-vitro/in-vivo characteristics of the prodrug AQ4N (for example, see U.S. Pat. No. 5,132,327).

The invention seeks to address the need for improved cancer treatments by providing novel anthraquinone compounds with a combination of preferable pharmacological and hypoxia-sensing properties.

SUMMARY

The first aspect of the invention provides a compound of Formula I

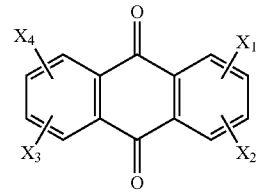

Formula I wherein $X_1$, $X_2$, $X_3$ and $X_4$ are each independently selected from the group consisting of hydrogen, hydroxy, halogeno, amino, $C_{1-4}$ alkoxy, $C_{2-8}$ alkanoyloxy, —NH-A-NHR, —NH-A-NR'R" and —NH-A-N(O) R'R"

wherein A is an alkylene group with a chain length of at least two carbon atoms (between NH and NHR or N(O)R'R"), wherein R, R' and R" are each independently selected from $C_{1-4}$ alkyl groups and $C_{2-4}$ hydroxyalkyl and $C_{2-4}$ dihydroxyalkyl groups in which the carbon atom attached to the nitrogen atom does not carry a hydroxy group and no carbon atom is substituted by two hydroxy groups, or wherein R and R" together are a $C_{2-6}$ alkylene group which with the nitrogen atom to which R' and R" are attached forms a heterocyclic group having 3 to 7 atoms in the ring, wherein at least one of $X_1$, $X_2$, $X_3$ and $X_4$ is selected from the group consisting of deuterated forms of —NH-A-NHR, —NH-A-NR'R" and —NH-A-N(O) R'R".

Thus, the invention provides novel deuterated anthraquinone compounds.

By "deuterated" we include that the compound comprises at least one atom of deuterium or heavy hydrogen (i.e. D or $^2$H). It will be appreciated by persons skilled in the art that the compound may be partially (i.e. selectively) or fully deuterated (i.e. containing hydrogen present only in the form of deuterium).

By "selectively", in this context, we mean that some but not all conventional $^1$H hydrogen atoms are replaced with deuterium. For example, one or more of substituent groups $X_1$, $X_2$, $X_3$ and $X_4$ may be deuterated while the central anthraquinone ring may be free of deuterium.

In one embodiment, the compound of the invention is selectively deuterated within one or more of substituent groups —NH-A-NHR, —NH-A-NR'R" and/or —NH-A-N(O)R'R" at positions $X_1$, $X_2$, $X_3$ and/or $X_4$. Within each such substituent group, it will be appreciated that A, R, R' and R" may be fully deuterated (i.e. thus containing no $^1$H) or may be partially deuterated.

In a preferred embodiment, the compound is deuterated only within one or more of the terminal groups R, R' and R". For example, R, R' and/or R" may represent:

$CD^3$;
$CH_2CD^3$;
$CD_2CD^3$;
$CD_2CH_2CD^3$; and
$CD_2CD_2\,CD_2CD^3$.

The term "$C_{1-4}$ alkyl" is intended to include linear or branched alkyl groups comprising between one and four carbons. Preferred alkyl groups which R, R' and/or R" may independently represent include $C_1$ and $C_2$ alkyl.

The term "lower alkylene" is to be construed accordingly.

The terms "$C_{2-4}$ hydroxyalkyl" and "$C_{2-4}$ dihydroxyalkyl" are intended to include linear or branched alkyl groups comprising between two and four carbons, to which are attached one or two hydroxy groups, respectively. For example, R, R' and/or R" may independently represent:

$CH_2CH_2OH$
$CH_2CH(OH)CH_3$
$CH_2CH_2CH(OH)CH_2OH$

The term "$C_{1-4}$ alkoxy" is intended to include linear or branched $C_{1-4}$ alkyl groups bound to the core anthraquinone (anthracene-9,10-dione) ring via oxygen. For example, R, R' and/or R" may independently represent:

$OCH_3$
$OCH_2CH_3$
$OCH_2CH_2CH_3$
$OCH_2CH_2CH_2CH_3$

The term "$C_{2-8}$ alkanoyloxy" is intended to include linear or branched $C_{2-8}$ alkanoyl groups bound to the core anthraquinone (anthracene-9,10-dione) ring via oxygen. For example, R, R' and/or R" may independently represent:

$O(O)CCH_3$
$O(O)CCH_2CH_3$
$O(O)CCH_2CH_2CH_3$
$O(O)CCH_2CH_2CH_2CH_3$
$O(O)CCH_2CH_2CH(CH_3)CH_3$

The term "hydroxy" is intended to represent —OH.

The term "halogeno" is intended to represent any halogen group, such as —Br, —Cl and —F.

The term "amino" is intended to include primary amine groups, such as —$NH_2$.

It will be appreciated by persons skilled in the art that the anthraquinone ring of the compounds may be substituted by $X_1$, $X_2$, $X_3$ and $X_4$ at any of ring positions 1, 2, 3, 4, 5, 6, 7 or 8:

In one embodiment of the first aspect of the invention, the compound is substituted at ring positions 1, 4, 5 and 8, in accordance with Formula II:

Formula II

In one embodiment, $X_1$, $X_2$, $X_3$ and $X_4$ are each separately selected from the group consisting of hydrogen, hydroxy, —NH-A-NHR, —NH-A-NR'R", —NH-A-N(O)R'R" and deuterated forms thereof.

In one embodiment, $X_1$, $X_2$, $X_3$ and $X_4$ are each separately selected from the group consisting of hydroxy, —NH-A-NR'R", —NH-A-N(O)R'R" and deuterated forms thereof.

In one embodiment, $X_1$ and $X_2$ are both hydroxy and $X_3$ and $X_4$ are both —NH-A-N(O)R'R" or deuterated forms thereof.

In one embodiment, $X_1$ and $X_2$ are both hydroxy and $X_3$ and $X_4$ are both NH-A-NR'R" or deuterated forms thereof.

In one embodiment, A is unbranched. For example, A may be ethylene.

In one embodiment, R, R' and R" are each independently selected from the group consisting of —$CH_3$, —$CH_2CH_3$, —$CH_2CH_2CH_3$, —$CH_2CH_2OH$, —$CH_2CH_2CH_2OH$, —$CH(CH_3)CH_2OH$, —$CH_2CHOHCH_2OH$ and deuterated forms thereof.

In one embodiment, one or two of $X_1$, $X_2$, $X_3$ and $X_4$ are independently selected from the group consisting of —NH—$(CH_2)_2$—N(O)$(CH_3)_2$, —NH—$(CH_2)_2$—N(O)$(CH_3)C_2H_5$, —NH—$(CH_2)_2$—N(O)$(C_2H_5)_2$, —NH—$(CH_2)_2$—N(O)$(CH_2CH_2OH)_2$, —NH—$(CH_2)_2$—N(O)$(CH_2CH_2CH_2OH)_2$, —NH—$(CH_2)_2$—N(O)CH$(CH_3)$OH, —NH—$(CH_2)_2$—N(O)$(CH_2CHOHCH_2OH)_2$ and deuterated forms thereof.

In one embodiment, one or two of $X_1$, $X_2$, $X_3$ and $X_4$ are independently selected from the group consisting of —NH—$(CH_2)_2$—N$(CH_3)_2$, —NH—$(CH_2)_2$—N$(CH_3)C_2H_5$, —NH—$(CH_2)_2$—N$(C_2H_5)_2$, —NH—$(CH_2)_2$—N$(CH_2CH_2OH)_2$, —NH—$(CH_2)_2$—N$(CH_2CH_2CH_2OH)_2$, —NH—$(CH_2)_2$—NCH$(CH_3)$OH, —NH—$(CH_2)_2$—N$(CH_2CHOHCH_2OH)_2$ and deuterated forms thereof.

In one embodiment, the compound of the invention comprises one group —NH-A-N(O)R'R" and one group —NH-A-NHR, the —NH-A-NHR group being selected from —NH—$(CH_2)_2$—NHCH$_3$, —NH—$(CH_2)_2$—NHC$_2$H$_5$, —NH—$(CH_2)_2$—NHCH$_2$CH$_2$OH, —NH—$(CH_2)_2$—NHCH$_2$CH$_2$CH$_2$OH, —NH—$(CH_2)_2$—NHCH$(CH_3)$CH$_2$OH, —NH—$(CH_2)_2$—NHCH$_2$CHOHCH$_2$OH and deuterated forms thereof.

In one embodiment, the compound of the invention comprises one group —NH-A-NR'R" and one group —NH-A-NHR, the —NH-A-NHR group being selected from —NH—(CH$_2$)$_2$—NHCH$_3$, —NH—(CH$_2$)$_2$—NHC$_2$H$_5$, —NH—(CH$_2$)$_2$—NHCH$_2$CH$_2$OH, —NH—(CH$_2$)$_2$—NHCH$_2$CH$_2$CH$_2$OH, —NH—(CH$_2$)$_2$—NHCH(CH$_3$)CH$_2$OH, —NH—(CH$_2$)$_2$—NHCH$_2$CHOHCH$_2$OH and deuterated forms thereof.

In preferred, but non-limiting, compounds of the invention:
(a) X$_1$=—NH-A-N(O)R'R", X$_2$=—H and X$_3$=X$_4$=—OH;
(b) X$_1$=—NH-A-N(O)R'R", X$_2$=—OH, X$_3$=—OH and X$_4$=—H;
(c) X$_1$=—NH-A-N(O)R'R" and X$_2$=X$_3$=X$_4$=—OH;
(d) X$_1$=X$_4$=—NH-A-N(O)R'R" and X$_2$=X$_3$=—OH;
(e) X$_1$=X$_2$=—NH-A-N(O)R'R" and X$_3$=X$_4$=—OH;
(f) X$_1$=X$_3$=—NH-A-N(O)R'R" and X$_2$=X$_4$=—OH;
(g) X$_1$=—NH-A-NR'R", X$_2$=—H and X$_3$=X$_4$=—OH;
(h) X$_1$=—NH-A-NR'R", X$_2$=—OH at position 4, X$_3$=—OH and X$_4$=—H;
(i) X$_1$=—NH-A-NR'R" and X$_2$=X$_3$=X$_4$=—OH;
(j) X$_1$=X$_4$=—NH-A-NR'R" and X$_2$=X$_3$=—OH;
(k) X$_1$=X$_2$=—NH-A-NR'R" and X$_3$=X$_4$=—OH;
(l) X$_1$=X$_3$=—NH-A-NR'R" and X$_2$=X$_4$=—OH;
and deuterated forms thereof.

In further preferred, but non-limiting, compounds of the invention:
(a) X$_1$=—NH-A-N(O)R'R", X$_2$=—NH-A-NHR, and X$_3$=X$_4$=—OH;
(b) X$_1$=—NH-A-N(O)R'R", X$_2$=—OH, X$_3$=—NH-A-NHR and X$_4$=—OH;
(c) X$_1$=—NH-A-N(O)R'R", X$_2$=X$_3$=—OH and X$_4$=—NH-A-NHR;
(d) X$_1$=—NH-A-NR'R", X$_2$=—NH-A-NHR, and X$_3$=X$_4$=—OH;
(e) X$_1$=—NH-A-NR'R", X$_2$=—OH, X$_3$=—NH-A-NHR and X$_4$=—OH;
(f) X$_1$=—NH-A-NR'R", X$_2$=X$_3$=—OH and X$_4$=—NH-A-NHR;
and deuterated forms thereof.

In further preferred, but non-limiting, compounds of the invention:
(a) X$_1$=X$_2$=—NH-A-N(O)R'R" and X$_3$=X$_4$=—OH;
(b) X$_1$=X$_3$=—NH-A-N(O)R'R" and X$_2$=X$_4$=—OH;
(c) X$_1$=X$_2$=—NH-A-NR'R" and X$_3$=X$_4$=—OH; and
(d) X$_1$=X$_3$=—NH-A-NR'R" and X$_2$=X$_4$=—OH
wherein
both —NH-A-N(O)R'R" are —NH—(CH$_2$)$_2$N(O)(CH$_3$)$_2$ or —NH—(CH$_2$)$_2$N(O)(CH$_2$CH$_2$OH)$_2$, or deuterated forms thereof and
both NH-A-NR'R" are —NH—(CH$_2$)$_2$N(CH$_3$)$_2$ or —NH—(CH$_2$)$_2$N(CH$_2$CH$_2$OH)$_2$, or deuterated forms thereof.

In further preferred, but non-limiting, compounds of the invention:
(a) X$_1$=—NH-A-N(O)R'R", X$_2$=—NH-A-NHR and X$_3$=X$_4$=—OH;
(b) X$_1$=—NH-A-N(O)R'R", X$_2$=—OH, X$_3$=—NH-A-NHR and X$_4$=—OH;
(c) X$_1$=—NH-A-NR'R", X$_2$=—NH-A-NHR and X$_3$=X$_4$=—OH; and
(d) X$_1$=—NH-A-NR'R", X$_2$=—OH, X$_3$=—NH-A-NHR and X$_4$=—OH,
wherein
—NH-A-N(O)R'R" is —NH—(CH$_2$)$_2$N(O)(CH$_3$)$_2$ or —NH—(CH$_2$)$_2$N(O)(CH$_2$CH$_2$OH)$_2$ or a deuterated form thereof —NH-A-NHR is NH—(CH$_2$)$_2$NHCH$_3$ or NH(CH$_2$)$_2$NHCH$_2$CH$_2$OH or a deuterated form thereof
and NH-A-NR'R" is —NH—(CH$_2$)$_2$N(CH$_3$)$_2$ or —NH—(CH$_2$)$_2$N(CH$_2$CH$_2$OH)$_2$ or a deuterated form thereof.

In one embodiment, the compound is of Formula III or IV:

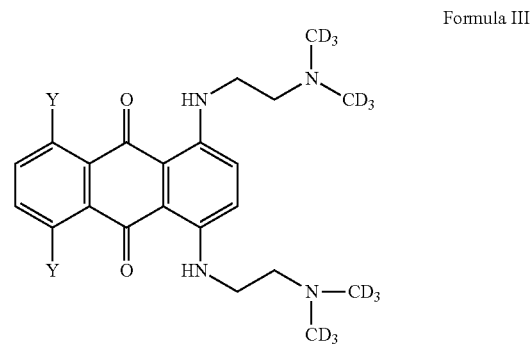

Formula III

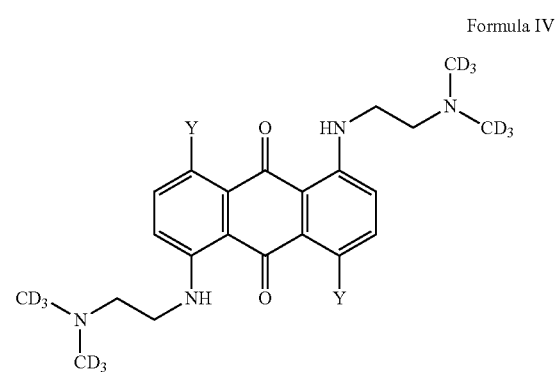

Formula IV wherein Y are each independently selected from the group consisting of hydrogen, hydroxy, halogeno, amino, C$_{1-4}$ alkoxy and C$_{2-8}$ alkanoxy, or a prodrug thereof.

By "prodrug", in this context, is included compounds which may readily be converted in vivo to a compound of Formula III or IV. In one embodiment, the conversion is triggered by the prodrug entering an hypoxic environment, such as a solid tumour.

Examples of suitable prodrugs include N-oxide derivatives of the compounds of Formula III or IV.

Thus, in one embodiment, the prodrug is a compound of Formula V or VI:

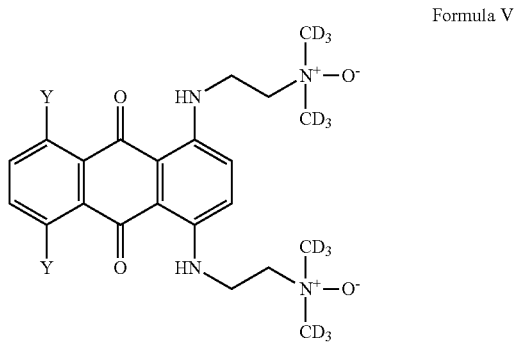

Formula V

Formula VI

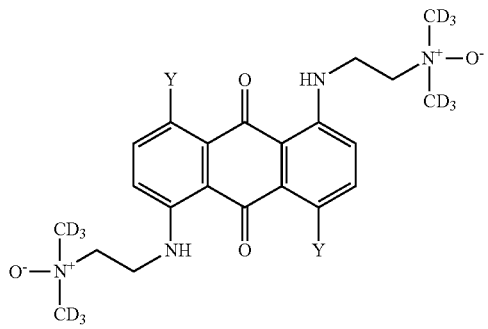

wherein Y are each independently selected from the group consisting of hydrogen, hydroxy, halogeno, amino, $C_{1-4}$ alkoxy and $C_{2-8}$ alkanoxy.

In one preferred embodiment, the compound is of Formula VII or VIII:

Formula VII

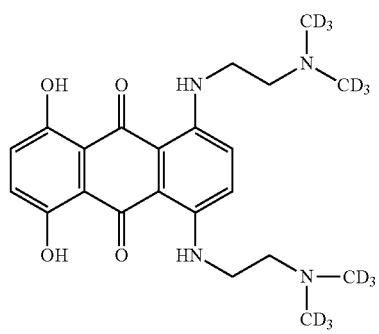

Formula VIII

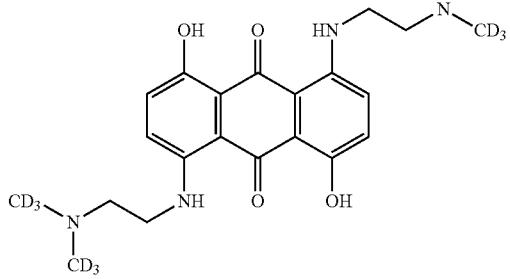

or a prodrug thereof.

In a further preferred embodiment, the compound is prodrug of Formula IX or X:

Formula IX

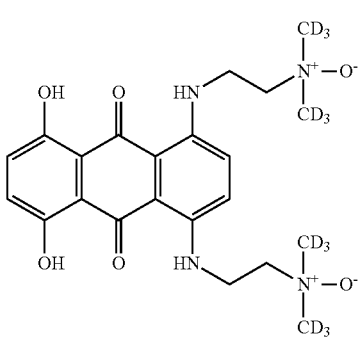

Formula X

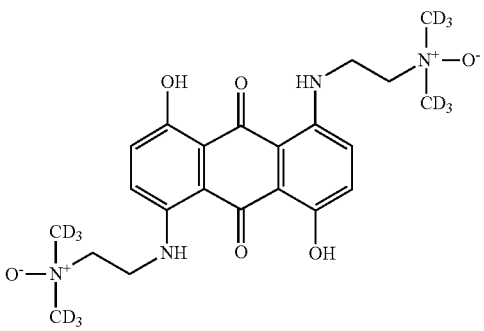

In the compounds of Formulae III to X, it will be appreciated by persons skilled in the art that one or more of the deuterium atoms in one or more of the methyl groups attached to the nitrogen of the terminal amino groups may be replaced by conventional hydrogen (i.e. $^1H$), provided that the compound comprises at least one deuterium atom. For example, one, two, three or four of the methyl groups may be $-CH_3$, $-CH_2D$ or $-CHD_2$. In one embodiment, the methyl groups in the compound are either-$CH_3$ or $-CD_3$.

It will be further appreciated by skilled persons that certain compounds of formulae I to X above may be counterbalanced by counter-anions. Exemplary counter-anions include, but are not limited to, halides (e.g. fluoride, chloride and bromide), sulfates (e.g. decylsulfate), nitrates, perchlorates, sulfonates (e.g. methane sulfonate) and trifluoroacetate. Other suitable counter-anions will be well known to persons skilled in the art. Thus, pharmaceutically, and/or veterinarily, acceptable derivatives of the compounds of formulae I to X, such as salts and solvates, are also included within the scope of the invention. Salts which may be mentioned include: acid addition salts, for example, salts formed with inorganic acids such as hydrochloric, hydrobromic, sulfuric and phosphoric acid, with carboxylic acids or with organo-sulfonic acids; base addition salts; metal salts formed with bases, for example, the sodium and potassium salts.

In one embodiment, the compound is in the form of a halide salt, for example a chloride salt.

It will be further appreciated by skilled persons that certain compounds of formulae I to X may exhibit tautomerism. All tautomeric forms and mixtures thereof are included within the scope of the invention.

Compounds of formulae I to X may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively, the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

Various routes are available for the synthesis of the compounds of the invention. One very convenient procedure for the preparation of compounds having a group —NH-A-NR'R" at the 1 and 4 positions uses the appropriately substituted 2,3-dihydro(leuco)-1,4-dihydroxyanthracene-9,10-dione which is condensed with the appropriate amine R"R'N--A--NH$_2$, the 1,4 positions being activated in the leuco compound for reaction with the amine. Such a condensation may conveniently be effected at a temperature in a range of about 25° C. or 35° C. to 50° C. or 60° C. for one or more hours using a solvent such as methanol, ethanol, water, dimethylformamide, 2-methoxyethanol, acetonitrile, nitrobenzene, N,N,N'N'-tetra-methylenediamine or mixtures thereof. In some instances a higher temperature and shorter reaction time may be appropriate, for example with the compounds containing cyclic groups NR'R". The leuco derivative is then oxidized to the fully aromatic anthracene-9,10-dione, conveniently using air oxidation or oxidation with hydrogen peroxide, chloranil, sodium perborate or manganese dioxide.

Although leuco compounds are primarily of interest for the preparation of compounds substituted by two —NH-A-NHR'R" groups, it is possible to use them to prepare compounds containing more than two such groups. Thus, by using 2,3-dihydro(leuco)-1,4,5,8-tetrahydroxyanthracene-9,10-dione and a large excess of an amine —NH-A-NHR'R" an 8-hydroxyanthracene-9,10-dione having three groups —NH-A-NHR'R" at the 1, 4 and 5 positions may be prepared.

The leuco derivatives themselves are obtainable by heat treatment of the corresponding fully aromatic 1,4-dihydroxyanthracene-9,10-dione, conveniently by heating at above 90° C. for 1 hour or more in a stream of nitrogen and, if necessary, in the presence of a suitable reducing agent such as sodium dithionite or zinc dust. Various anthracene-9,10-diones, particularly hydroxyanthracene-9,10-diones, are commercially available and various syntheses for such compounds are also reported in the literature. One suitable procedure for their preparation involves the reaction of an appropriately substituted phthalic anhydride with hydroquinone in the presence of aluminium chloride and sodium hydroxide at 180° C. for one hour or more. Anthracene-9,10-diones containing one form of substituent group can be modified to provide other forms of substituent group so that, for example, a dione containing an amino group can be treated with sodium hydroxide/dithionite to yield the corresponding hydroxy substituted compound.

Other suitable procedures for the preparation of intermediates for oxidation to the N-oxide compounds of the invention include the reaction of the appropriate chloro or fluoro substituted anthracene-9,10-dione with the appropriate amine R"R'N--A--NH2, for example by heating with a excess of the amine at its reflux temperature for one or more hours. Certain of these chloro- and fluoro anthracene-9,10-diones are known and various syntheses for such compounds are also reported in the literature. Thus, for example, a KF—NaF-mediated conversion of 3,6-dichlorophthalic anhydride to 3,6-difluorophthalic anhydride as a precursor to making 1,4-difluoro-4,8-dihydroxyanthracene-9,10-dione (see Lee & Denny, 1999, *J. Chem. Soc., Perkin Trans.* 1:2755-2758. Additionally, for example, 1,5-dichloro-4,8-dihydroxyanthracene-9,10-dione may be prepared by selective chlorination of 1,4,5,8-tetrahydroxyanthracene-9,10-dione using a stoichiometric amount of sulphuryl chloride and controlled temperature. This precursor may then be used to prepare an intermediate having groups —NH-A-NR'R" at the 1 and 5 positions and hydroxy groups at the 4 and 8 positions, the hydroxy groups conveniently being protected during the reaction with the amine R"R'N--A--NH$_2$. A similar approach is suitable for the preparation of other chlorohydroxyanthracene-9,10-dione intermediates.

Where the compound of the invention contains one or more groups —NH-A-NHR in addition to the one or more groups —N-A-NR'R" the compound may conveniently be produced by reacting a suitable precursor as discussed above with a mixture of amines RN--A--NH.sub.2 and R"R'N--A--NH.sub.2, the resultant mixture of products then being separated, for example by chromatography. Thus, for example, 2,3-dihydro(leuco)-1,4-dihydroxyanthracene-9,10-dione on reaction with a mixture of 2-(2-hydroxyethylamino)ethylamine and 2-(diethylamino)ethylamine will yield a mixture of 1,4-bis{[2-(diethylamino)-ethyl]amino}anthracene-9,10-dione, 1,4-bis{[2-(2-hydroxyethylamino)-ethyl]amino}-anthracene-9,10-dione and 1-(2-(diethylamino)ethyl]amino)-4-{[2-(2-hydroxyethylamino)-ethyl]amino}anthracene-9,10-dione from which the last mentioned compound may be separated, for example by chromatography. On oxidation, only the tertiary nitrogen atom of the [2-(diethylamino)ethyl)] amino group will be converted to N-oxide form.

Where one or more substituent groups is present it may be appropriate, depending on the route of synthesis, to have these present throughout in their final form or to generate the desired groups at a later stage in the synthesis. Ether and ester groups X may of course readily be prepared by modification of hydroxy groups according to known procedures, precursors containing a hydroxy group X more often being described in the literature than those containing a corresponding ether or ester substituent.

It will be appreciated, however, that various alternative methods for the preparation of the compounds and intermediates therefor may be used as will be apparent in particular from the literature relating to such intermediates. Further details of the preparation of intermediates for the preparation of the compounds of the present invention are to be found in U.S. Pat. No. 4,197,249 and GB 2,004,293B (the disclosures of which are incorporated herein by reference).

Thus, a second aspect of the invention provides a process for making a compound according to the first aspect of the invention comprising reacting an anthracene-9,10-dione with a deuterated alkylenediamine under conditions suitable for the production of an alkylaminoalkylaminoanthraquinone.

Optionally, the process further comprises the step of reacting the alkylamino-alkylaminoanthraquinone with a monoperoxyphthalate to under conditions suitable for the production of an N-oxide derivative of the alkylaminoalkylaminoanthraquinone.

In one embodiment, the process comprises reacting 1,4-difluoro-5,8-dihydroxyanthracene-9,10-dione, 281-005 with deuterated--N,N-dimethylethylenediamine under conditions suitable for the production of 1,4-bis-{[2-(deuterated-d6-dimethylamino)ethyl]amino}-5,8-dihydroxyanthracene-9,10-dione.

In a further embodiment, the process comprises the step of reacting the 1,4-bis-{[2-(deuterated-d6-dimethylamino)ethyl]amino)-5,8-dihydroxyanthracene-9,10-dione with magnesium monoperoxyphthalate under conditions suitable for the production of 1,4-bis-{[2-(deuterated-d6-dimethylamino-N-oxide)ethyl]amino)-5,8-dihydroxy-anthracene-9,10-dione.

A third aspect of the invention provides a pharmaceutical composition comprising a compound according to the first aspect of the invention together with pharmaceutically acceptable buffer, diluent, carrier, adjuvant or excipient.

By "pharmaceutically acceptable" we include a non-toxic material that does not decrease the therapeutic effectiveness of the compound of the invention. Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000), the disclosures of which are incorporated herein by reference).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the agent in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the compound of the invention. The adjuvant may be one or more of zinc, copper or silver salts with different anions, for example, but not limited to fluoride, chloride, bromide, iodide, thiocyanate, sulfite, hydroxide, phosphate, carbonate, lactate, glycolate, citrate, borate, tartrate, and acetates of different acyl composition. The adjuvant may also be cationic polymers such as cationic cellulose ethers, cationic cellulose esters, deacetylated hyaluronic acid, chitosan, cationic dendrimers, cationic synthetic polymers such as poly(vinyl imidazole), and cationic polypeptides such as polyhistidine, polylysine, polyarginine, and peptides containing these amino acids.

The excipient may be one or more of carbohydrates, polymers, lipids and minerals. Examples of carbohydrates include lactose, glucose, sucrose, mannitol, and cyclodextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The compounds of the invention may be formulated into any type of pharmaceutical composition known in the art to be suitable for the delivery thereof.

In one preferred embodiment, the pharmaceutical compositions are administered parenterally, for example, intravenously, intracerebroventricularly, intraarticularly, intraarterially, intraperitoneally, intrathecally, intraventricularly, intrasternally, intracranially, intramuscularly or subcutaneously, or they may be administered by infusion techniques. The pharmaceutical compositions may also administered intra-tumourally and/or peri-tumourally.

Such pharmaceutical compositions are conveniently used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

In a further embodiment, the pharmaceutical compositions of the invention may be in the form of a liposome, in which the agent is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Suitable lipids also include the lipids above modified by poly(ethylene glycol) in the polar headgroup for prolonging bloodstream circulation time. Preparation of such liposomal formulations is can be found in for example U.S. Pat. No. 4,235,871, the disclosures of which are incorporated herein by reference.

The pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly(caprolactone) (PCL), and polyanhydrides have been widely used as biodegradable polymers in the production of microspheres. Preparations of such microspheres can be found in U.S. Pat. No. 5,851,451 and in EP 0 213 303, the disclosures of which are incorporated herein by reference.

In a further embodiment, the pharmaceutical compositions of the invention are provided in the form of polymer gels, where polymers such as starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polyvinyl imidazole, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone are used for thickening of the solution containing the agent. The polymers may also comprise gelatin or collagen.

Alternatively, the compounds may simply be dissolved in saline, water, polyethylene glycol, propylene glycol, ethanol or oils (such as safflower oil, corn oil, peanut oil, cottonseed oil or sesame oil), tragacanth gum, and/or various buffers.

It will be appreciated that the pharmaceutical compositions of the invention may include ions and a defined pH for potentiation of action of the active agent. Additionally, the compositions may be subjected to conventional pharmaceutical operations such as sterilisation and/or may contain conventional adjuvants such as preservatives, stabilisers, wetting agents, emulsifiers, buffers, fillers, etc.

The pharmaceutical compositions according to the invention may be administered via any suitable route known to those skilled in the art. Thus, possible routes of administration include parenteral (intravenous, subcutaneous, and intramuscular), topical, ocular, nasal, pulmonar, buccal, oral, parenteral, vaginal and rectal. Also administration from implants is possible.

Alternatively, the pharmaceutical compositions may be administered intranasally or by inhalation (for example, in the form of an aerosol spray presentation from a pressurised container, pump, spray or nebuliser with the use of a suitable propellant, such as dichlorodifluoromethane, trichlorofluoro-methane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas). In the case of a pressurised aerosol, the dosage unit may be determined by providing a valve to deliver a metered amount. The pressurised container, pump, spray or nebuliser may contain a solution or suspension of the active polypeptide, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

The pharmaceutical compositions will be administered to a patient in a pharmaceutically effective dose. A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art. The administration of the pharmaceutically effective dose can be carried out both by single administration in the form of an individual dose unit or else several smaller dose units and also by multiple administrations of subdivided doses at specific intervals. Alternatively, the dose may be provided as a continuous infusion over a prolonged period.

It will be appreciated that the compositions of the invention may be formulated in unit dosage form, i.e. in the form of discrete portions containing a unit dose or a multiple or sub-unit of a unit dose.

Whilst the dosage of the compound used will vary according to the activity of the particular compound and the condition being treated, it may be stated by way of guidance that a dosage selected in the range from 0.1 to 20 mg/kg per body weight per day, particularly in the range from 0.1 to 5 mg/kg of body weight per day, will often be suitable although higher doses than this, for example in the range from 0.1 to 50 mg/kg of body weight per day (or possibly even as high as described in U.S. Pat. No. 4,197,249) may be considered in view of the lower level of toxic side effects obtained with the compounds. This dosage regime may be continued for however many days is appropriate to the patient in question, the daily dosages being divided into several separate administrations if desired. Thus, for example, in the case of conditions such as advanced breast cancer, non-Hodgkin's lymphoma and hepatoma, treatment for one day followed by a repeated dose after an interval, such as 21 days, may be appropriate whilst for the treatment of acute non-lymphocytic leukaemia, treatment over 5 consecutive days may be more suitable.

A fourth aspect of the invention provides a compound according to the first aspect of the invention for use in medicine (clinical and/or veterinary).

A fifth aspect of the invention provides a compound according to the first aspect of the invention for use as a cytotoxin, or a hypoxia activated prodrug thereof.

In one embodiment, the compound is for use in vivo as a cytotoxin, or a hypoxia activated prodrug thereof.

By "hypoxia activated prodrug thereof" we include that the compound is preferentially cytotoxic under, or following exposure to, hypoxic conditions (i.e. exhibits greater cytotoxicity under, or following exposure to, hypoxic conditions). For example, N-oxide compounds of the invention, such as those of formulae V, VI, IX and X, are relatively non-cytotoxic under normoxic conditions but are readily reduced under hypoxic conditions to generate cytotoxic compounds, such as those of formulae III, IV, VII and VIII.

In this context, "hypoxia" may be regarded as an oxygenation level of 4% or lower (or ≤23 mmHg) when measured directly by electrode methods. For example, the level of oxygenation may be lower than 3.0%, 2.5%, 2%, 1.5%, 1% or 0.5 or 0.1%.

It will be appreciated by persons skilled in the art that the hypoxia-induced activation of a compound's cytotoxic activity may be determined either in vitro or in vivo.

For example, cytotoxicity may be determined in vitro at various oxygenation levels measured by direct electrode methods.

Alternatively, the level of oxygenation in a tissue may be measured indirectly, for example using histological sections probed with an enzyme detection assay or by gene expression analysis.

For confirmation of hypoxia-activated cytotoxicity in vivo, oxygenation levels in living tissue may be determined using both the Helzel and OxyLite systems (for example, see Wen et al., 2008, Radiat. Res. 169:67-75).

The results of blood flow and perfusion analyses may also infer the existence of hypoxia in a given tissues. The application of agents that modify blood flow or compromise blood vessel formation would also on first principles be expected to reduce oxygenation in affected tissues.

In particular, the invention provides a compound according to the first aspect of the invention for use in the treatment of cancer in mammals (most notably in humans).

For example, the compound may be for use in the treatment of a cancer selected from the group consisting of bladder cancer, breast cancer, bone cancer (primary and secondary, such as osteosarcoma and Ewings sarcoma), brain cancer (including glioblastoma multiforme and astrocytoma), cervical cancer, choriocarcinoma, colon and rectal cancer, endometrial cancer, eye cancer, gallbladder cancer, gastric cancer, gestational tumours, head and neck cancer, kidney (renal cell) cancer, laryngeal cancer, leukaemias (such as ALL, AML, CLL, CML and hairy cell leukaemias), liver cancer, lung cancer, lymphomas (such as Hodkin's lymphoma and non-Hodkin's lymphoma), melanoma, mesothelioma, mouth cancer, myeloma, nasal and sinus cancers, nasopharyngeal cancer, oesophageal cancer, ovarian cancer, pancreatic cancer, penile cancer, prostate cancer, stomach cancer, testicular cancer, thyroid cancer, uterine cancer, vaginal cancer, vulvar cancer and womb cancer.

In one embodiment, the compound is for use in the treatment of a solid tumour, such as various forms of sarcoma and carcinoma.

The compounds of the invention may be of particular use in the treatment of a tumour that is naturally hypoxic, at least in part (for example, having a median oxygen level of below 3%, e.g. lower than 2.5%, 2%, 1.5%, 1% or 0.5%). An example of such tumours are pancreatic cancer and prostate cancer, both typically exhibiting low oxygen levels and a propensity for malignant progression.

The hypoxia-activated cytotoxicity of the prodrug compounds of the invention allows the cytotoxicity to be targeted to the tumour cells, reducing the risk of damage to healthy cells.

It is believed that hypoxia may play a role in facilitating the malignant progression of certain cancers (for example, see Rudolfsson & Bergh, 2009, *Exp. Opin. Ther. Tar.* 13:219-225). By exerting a cytotoxic effect preferentially within the regions of tumour hypoxia, the compounds of the invention may be able to target cancer cells that are otherwise resistant to treatment, e.g. by radiotherapy or conventional chemotherapeutic agents. Eradication of such resistant cells may, in turn, lead to a reduction in metastasis.

Thus, in one embodiment, the compounds are for use in the treatment or prevention of metastases (which may arise from the aetiology of the cancer or as a consequence of treatment).

It will be appreciated by persons skilled in the art that the compounds of the invention may be used on their own or in combination with other cancer treatments (such as radiotherapeutic modalities, e.g. radioisotopes and external beam radiation, and chemotherapeutic agents; see below).

In one embodiment, the compounds are for use as a monotherapy (i.e. without any other cancer treatments).

However, it will be appreciated that the cancer patient may also be receiving different types of beneficial medication (such as a painkiller, sedative, antidepressant, antibiotic, etc).

However, the compounds of the invention may alternatively be for use in combination with one or more additional cancer treatments. For example, the compounds may be used in combination with one, two, three, four, five or more additional cancer treatments.

By "in combination" we include that the compound is administered to a subject who is receiving one or more additional cancer treatments in the same course of therapy. Thus, the term covers not only the concomitant administration of the compound with one or more additional cancer treatments (either as bolus doses or infusions) but also the temporally separate administration of these cancer treatments. For example, the compound may be administered within a treatment schedule/cycle as defined by the patient's oncologist to include one or more additional cancer treatments, administered either before, concomitantly with or after the compound; for example within ten weeks, nine weeks, eight weeks, seven weeks, six weeks, five weeks, four weeks, three weeks, two week, ten days, one week, five days, four days, three days, two days, one day, 12 hours, 10 hours, 8 hours, 6 hours, 4 hours, 3 hours, 2 hours, 1 hour, 45 minutes, 30 minutes, 20 minutes, 10 minutes or five minutes. Each treatment cycle may be repeated on several occasions, normally up to 6 cycles, but could be more or less than this number depending on the nature of the cancer and its response to treatment.

It will be appreciated by persons skilled in the art that the one or more additional cancer treatments may be chemotherapeutic agents or radiotherapeutic modalities.

In one embodiment, however, the one or more additional cancer treatments comprise or consist of one or more chemotherapeutic and/or radiotherapeutic modality.

Given the hypoxia-activated cytotoxicity of the prodrug compounds of the invention, it is advantageous to administer them as part of a combination treatment with one or more chemotherapeutic agents and/or radiotherapeutic modalities capable of decreasing (at least, transiently) tumour oxygenation levels in vivo. For example, the one or more chemotherapeutic agents and/or radiotherapeutic modalities may be capable of lowering the median oxygen level of the tumour to below 3%, for example below 2.5%, 2%, 1.5%, 1%, 0.5%, 0.4%, 0.3%, 0.2% or below 0.1%.

It will be appreciated by skilled persons that a reduction in tumour oxygenation levels may be achieved by a number of different means, for example by the disruption of established tumour vasculature, prevention of angiogenesis (new blood vessel formation) and/or vasoconstriction.

Suitable cancer treatments may be selected from the group consisting of anti-androgens (steroidal and non-steroidal), vascular disrupting agents, anti-angiogenic agents, anti-VEGFR agents, IL8 inhibitors, NO synthase inhibitors, vasoconstricting agents, vasodilating agents and radiotherapy.

By "steroidal anti-androgens" we include cyproterone acetate.

By "anti-angiogenic agents" we include:
(a) anti-VEGF antibodies or antibody fragments such as bevacizumab, axitinib, pazopanib and ranibizumab, pegaptanib sodium, tryptophanyl-tRNA synthetase, AdPEDF, EYLEA, AG-013958, JSM6427, TG100801, ATG3, rapamycin, endostatin;

(b) drugs that block signalling within the cell such as lapatinib, sunitinib, sorafenib, axitinib, pazopanib and AZ2171;

(c) tetrahydrocannabinol (THC) and cannabidiol;

(d) thiazolidinediones such as rosiglitazone, pioglitazone and troglitazone (e) erlotinib, imatinib, gefitinib, dasatinib, nilotinib, lapatinib; and (f) drugs that affect signals between cells, such as thalidomide and lenalidomide.

By "vascular disrupting agents" we include small molecules (such as taxanes, taxol, paclitaxel combretastatins, CA4P, Oxi4503, aurostatins, dolostatins, colchine, azacolchicinol, ZD6126I, MMP-activated colchicines, ICT2588, DMXAA, TZT1027 and AVE8062) and biologicals (such as ADEPT, GDEPT and antibody drug-conjugates that target the tumour vasculature).

By "IL8 inhibitors" we include repertaxin.

By "NO synthase inhibitors" we include NG-methyl-l-arginine hydrochloride (546C88; 1-NMMA), NG-nitro-L-arginine (L-NNA), L-nitroarginine methyl ester (L-NAME), LG-nitro-L-arginine (L-NO-Arg) and 7-Nitro-Indazole (7-NI).

By "vasoconstricting agents" we include alpha 1 adrenoceptor agonists (e.g. methoxamine, phenylephrine, oxymetazoline, tetrahydralazine, xylometazoline), alpha 2 adrenoceptor agonists (e.g. clonidine, guanabenz, guanfacine, α-methyldopa) and vasopressin analogues (e.g. arginine vasopressin and triglycyl lysine vasopressin).

By "vasodilating ('vascular steal') agents" we include alpha-adrenoceptor antagonists (alpha-blockers), angiotensin converting enzyme (ACE) inhibitors, angiotensin receptor blockers (ARBs), beta2-adrenoceptor agonists (β2-agonists), calcium-channel blockers (CCBs), centrally acting sympatholytics, direct acting vasodilators, endothelin receptor antagonists, ganglionic blockers, nitrodilators, phosphodiesterase inhibitors, potassium-channel openers and renin inhibitors.

By "radiotherapy modalities" we include conventional external beam radiation therapy (2DXRT), stereotactic radiosurgery (SRS), stereotactic body radiation therapy (SBRT) and particle therapy such as proton therapy; brachytherapy such as SAVI™, MammoSite™, Contura™, Proxcelan™, TheraSeed™ and I-Seed™; radioisotope therapy such as metaiodobenzylguanidine (MIBG), iodine-131, hormone-bound lutetium-177 and yttrium-90 (peptide receptor radionuclide therapy).

In one preferred embodiment, the one or more cancer treatments is/are non-steroidal anti-androgens, such as flutamide, nilutamide, bicalutamide, finasteride, dutasteride, bexlosteride, izonsteride, turosteride, episteride and abiraterone.

Thus, in one embodiment, a compound according to the first aspect of the invention is used in combination with bicalutamide in the treatment of cancer, e.g. the prevention or reduction of metastasis.

Thus, in one embodiment, a compound according to the first aspect of the invention is used in combination with cancer chemotherapeutic agents and/or radiotherapeutic modalities and/or methods to reduce or increase the air being breathed by the patients e.g. carbogen (with or without nicotinamide).

A related, sixth aspect of the invention provides the use of a compound of the first aspect of the invention in the preparation of a medicament for treating cancer.

Preferred embodiments of the sixth aspect of the invention are described above in relation to the fifth aspect of the invention.

A seventh aspect of the invention provides a method of treating cancer in a patient comprising administering to the patient a therapeutically effective amount of a compound of the first aspect of the invention.

In one embodiment, the patient is mammalian (e.g. human).

Preferred embodiments of the seventh aspect of the invention are described above in relation to the fifth aspect of the invention.

An eighth aspect of the invention provides the use of a compound of the first aspect of the invention as a marker of the oxygenation level of cells. In particular, such compounds may be used as a cellular hypoxic marker, either in vitro or in vivo.

In one embodiment, the cells are mammalian (e.g. human).

Exposure of the N-oxide forms of the compounds of the invention (such as those of formulae V and VI) to hypoxic cells causes their reduction to the corresponding amine form (such as those of formulae III and IV), which can be readily detected by known means.

The presence of the reduced compound (such as those of formulae III and IV) can be used to detect hypoxic cells in vitro or in vivo. The innate fluorescence properties retained by the reduced compound(s) and the intracellular persistence of the reduced compound(s) are advantageous for the discrimination, quantification and localisation of cells that have been exposed to, or continue to be exposed to hypoxic conditions.

For example, when acting as a cellular marker for hypoxia, the reduced compound (such as those of formulae III and IV) maybe detected using method(s) that identify chemical composition or physical properties that include but are not limited to mass spectrometry, infrared spectroscopy, colorimetry, Raman spectroscopy, nuclear magnetic resonance or positron emission tomography. Affinity capture methods would exploit the high affinity binding potential of the reduced compound to DNA or synthetic polynucleotide sequences.

Optical properties of the reduced compound(s) may be used to detect compound in biological samples and include but are not limited to flow cytometry and microscopy utilising the innate fluorescent properties of the reduced compound. Secondary methods of detection of reduced compound include but are not limited to a combination with other molecular reporter compounds with the reduced compound participating in resonant energy transfer reactions as either an acceptor or donor. Other secondary methods of detection of reduced compound include but are not limited to methods using antibody based methods for molecular detection.

In one embodiment, the compounds of the invention are used to identify hypoxic tumour cells in vivo, which may then be visualised in situ or excised surgically.

In a further embodiment, a compound of the first aspect of the invention is used as a cellular hypoxic marker in combination with a non-deuterated form of a compound of the first aspect of the invention.

By "in combination" in this context this includes that the compounds may be applied to the cells (e.g. administered to a patient) either concomitantly or sequentially (for example, within 24 hours, 12 hours, 6 hours, 4 hours, 3 hours, 2 hours, 1 hour, 30 minutes, 30 minutes, 10 minutes or less).

Thus, in a preferred embodiment, a compound of formulae IX or X is used as a cellular hypoxic marker (in vivo or in vitro) in combination with a compound as disclosed in U.S. Pat. No. 5,132,327 (for example, AQ4N).

A related, ninth aspect of the invention provides a kit of parts for use in detecting the oxygenation level of cells comprising a compound according to the first aspect of the invention.

Optionally, the kit further comprises a non-deuterated form of a compound according to the first aspect of the invention (such as a compound as disclosed in U.S. Pat. No. 5,132,327, for example AQ4N).

Preferably, the compound(s) is/are provided in a sterile, pyrogen-free form.

It will be appreciated that the kits of the invention may further comprise one or more regents, control samples and/or instructions.

Preferred, non-limiting examples which embody certain aspects of the invention will now be described, with reference to the following figures:

DETAILED DESCRIPTION OF THE EMBODIMENTS

Examples

Figure 1:
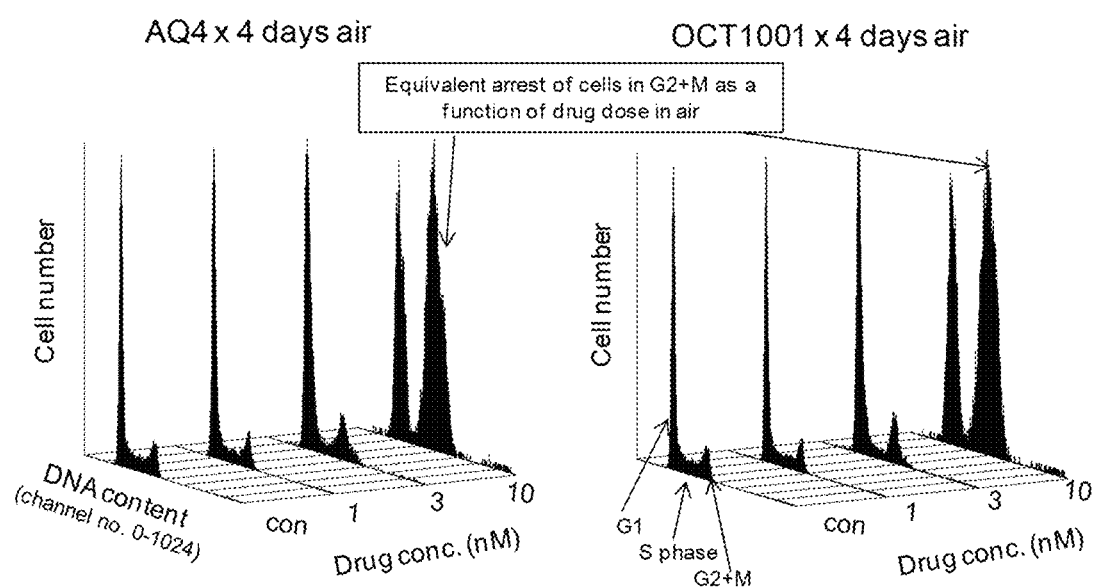
FIG. 1: The metabolites AQ4 and OCT1001 have similar cell cycle arresting actions, under normal oxygenation conditions, indicating that selective deuteration has not modified intrinsic biological activity.
See Example B

Example A: Synthesis of Alkylaminoalkylaminoanthraquinones and their N-Oxides (a) Preparation of 1,4-difluoro-5,8-dihydroxyanthracene-9,10-dione

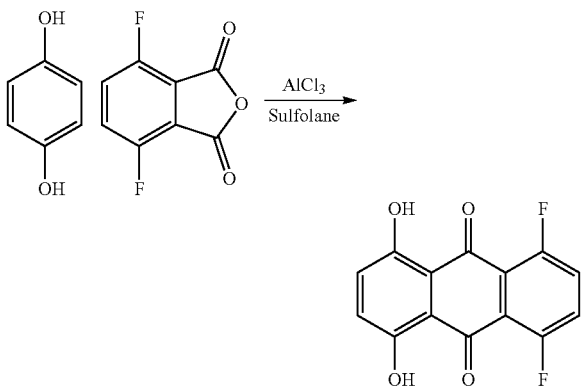

A mixture of 4,7-difluoroisobenzofuran-1,3-dione (8.50 g, 46.2 mmol), hydroquinone (5.64 g, 51.3 mmol), aluminium trichloride (36.9 g, 277 mmol) and sulfolane (10 mL) was stirred together for 16 hours at 165° C. The reaction was effectively a melt as the mixture does not become a viscous red syrup until ~150° C. To minimise the risk of a sudden exotherm and evolution of HCl gas, the reaction was stirred in portions, cooled in an ice bath and stirred again until mixing was sufficient. Only then was the mixture heated.

The mixture was poured carefully into ice and 2M HCl added (50 mL). The mixture was stirred, then filtered, washing the resultant slurry with further 2M HCl. The solid was re-slurried a further 3 times with 2M HCl to reduce the aluminium content of the product. A final slurry was washed with ether twice; drying in a round bottom flask at 60° C. until constant weight afforded 1,4-difluoro-5,8-dihydroxy-anthracene-9,10-dione (9.82 g, 35.6 mmol, 77% yield).

$^1$H NMR (DMSO-d$^6$) was clean and consistent with the desired material.

(b) Preparation of 1,4-bis-{[2-(deuterated-d6-dimethylamino)ethyl]amino)-5,8-dihydroxy-anthracene-9,10-dione

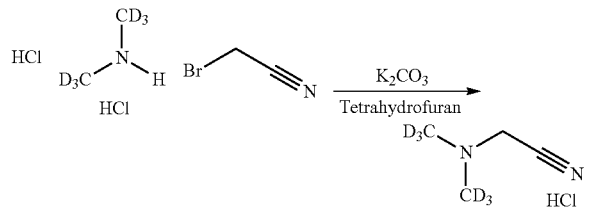

A suspension of deuterated-d6-dimethylamine hydrochloride (18.4 g, 210 mmol) and 2-bromoacetonitrile (14.63 ml, 210 mmol) in anhydrous THF (250 mL) in a round bottom flask was cooled to −10° C. with vigorous stirring and treated portion-wise with potassium carbonate (58.1 g, 420 mmol). After addition of the base, the reaction was fitted with a reflux condenser and balloons and allowed to warm slowly to 5° C. over 2 hours. TLC (1:1 EtOAc/Iso-Hexanes) indicated the presence of product. The mixture was stirred at room temperature over a weekend.

The residue was diluted with DCM (250 mL) and filtered, washing with copious amounts of DCM. The mother liquors were degassed with N$_2$ for 1 hour, then reduced in volume by half on the rotavap. Then a 4M dioxane solution of hydrogen chloride (52.5 ml, 210 mmol) was added, precipitating a white solid and the mixture allowed to stand for 10 minutes before being filtered, washing with DCM to afford deuterated-d6-dimethylacetonitrile (21.73 g, 172 mmol, 82% yield).

$^1$H NMR (400 MHz, d$_6$-DMSO) δ: 4.47 (2H, s) was consistent with the desired material.

(c) Preparation of deuterated-d6-N,N-dimethylethylenediamine

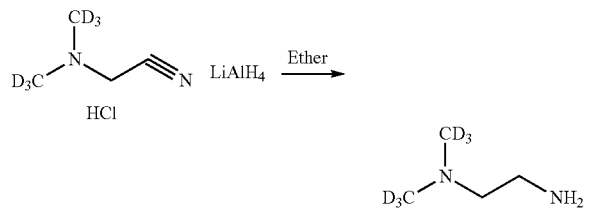

To a stirred suspension of deuturated-d6-dimethylacetonitrile (21.72 g, 172 mmol) in Et$_2$O (200 mL) at 0° C. was added d/w a 1M ether solution of lithium aluminium hydride (515 ml, 515 mmol) via dropping funnel over 1.5 hours. After the addition, the cooling bath was removed. After a further 1.5 hr, the reaction was quenched at 15° C. (no higher than 18° C.) with sodium sulfate decahydrate (0.5 eq rel. to LiAlH4, 80 g) cautiously (delayed reaction) over 1.5 hours. The mixture was left to stir for 1 hour and subsequently filtered, washing with ether. The filtrate was stored overnight in the dark. The ether was removed on the rotavap at ~40° C. with no vacuum to afford deuterated-d6-N,N-dimethylethylenediamine (15.89 g, 160 mmol, 93% yield was clean and consistent with the desired material but contained ~0.25 eq ether).

$^1$H NMR (400 MHz, CDCl$_3$) δ: 2.76 (2H, t), 2.33 (2H, t)

(d) Preparation of 1,4-bis-{[2-(deuterated-d6-dimethylamino)ethyl]amino)-5,8-dihydroxy-anthracene-9,10-dione ("OCT1001")

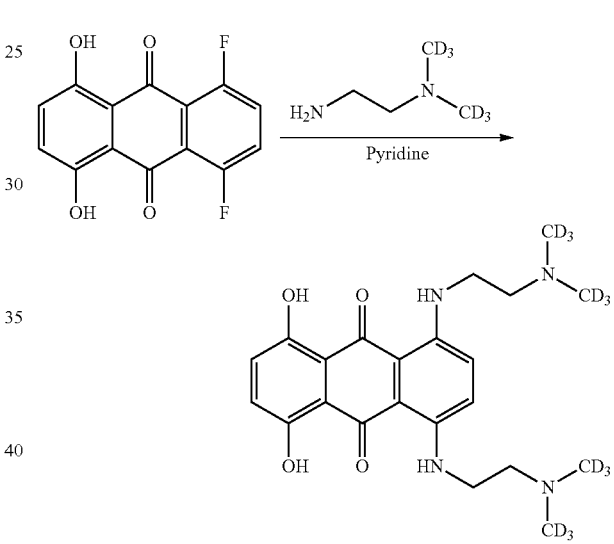

A solution of 1,4-difluoro-5,8-dihydroxyanthracene-9,10-dione, (4.9 g, 17.74 mmol) in pyridine (35 mL) was treated with deuterated-d6-N,N-dimethylethylenediamine, (16.57 ml, 142 mmol) as a steady stream. The mixture was warmed to 40° C. and allowed to stir for 24 hours under a flow of nitrogen. The reaction was taken off heat and cooled in an ice-bath. A chilled mixture of ammonium hydroxide (30%, 30 mL) and brine (30 mL) were added and the mixture stirred in an ice-bath for 2 hours. After this time the mixture was filtered washing with a 10% ammonium hydroxide solution (130 mL). The solid was air-dried for 30 minutes, then transferred to a tared flask and dried under vacuum at 60° C. until constant weight (~2 h).

The bulk material was purified by flash chromatography (Biotage, 120 g) loading in DCM (through cotton wool plug) eluting with 6 then 10% MeOH (containing 1% NH3)/DCM to give 1,4-bis-{[2-(deuterated-d6-dimethylamino)ethyl]amino)-5,8-dihydroxyanthracene-9,10-dione (2.01 g, 4.73 mmol, 26.7% yield).

The product was analysed by LCMS (m/z 425.3 (M+H)$^+$ (ES$^+$); 423.2 (M−H)− (ES)−, at 0.90 and 1.03 min (product smears on column), 100%.

¹H NMR (CDCl₃) was clean and consistent with the desired material ¹H NMR (400 MHz, CDCl₃) δ: 13.51 (2H, s), 10.40 (2H, br t), 7.17 (2H, s), 7.11 (2H, s), 3.47 (4H, q), 2.66 (4H, t).

(e) Preparation of 1,4-bis-{[2-(deuterated-d6-dimethylamino-N-oxide)ethyl]amino)-5,8-di-hydroxyanthracene-9,10-dione ("OCT1002")

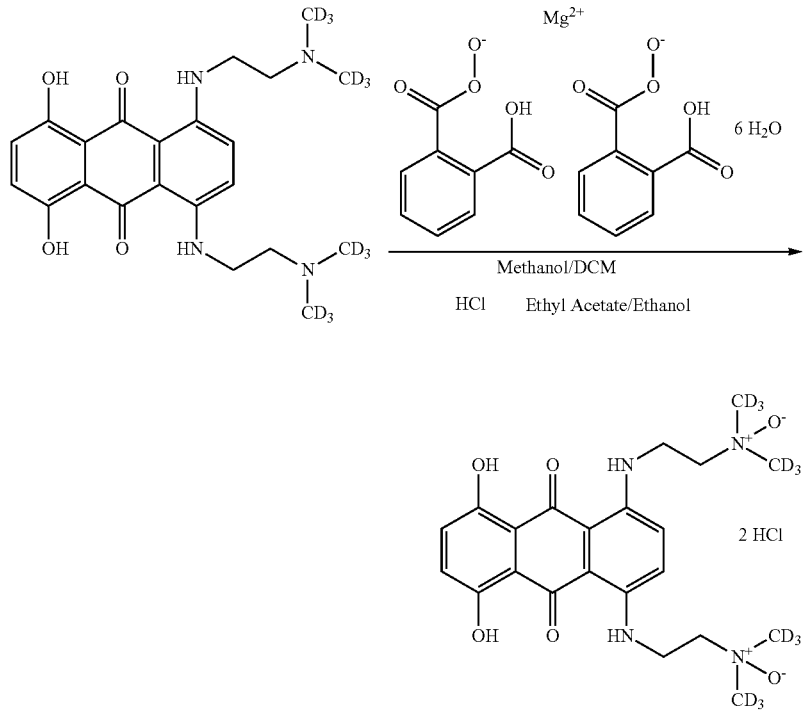

A suspension containing magnesium monoperoxyphthalate, MMPP (3.10 g, 6.27 mmol) in methanol (8 mL) was added dropwise to a stirred solution of 281-041 (1.90 g, 4.48 mmol), AQ4 in methanol (8 mL) and DCM (30 mL) cooled to −11° C. After the addition was complete, the reaction solution was allowed to warm to 0° C. and stirred overnight in the dark (warmed to room temperature during this time). Pre-cooled EtOAc (30 mL) and EtOH (6 mL) were added the reaction mixture at 0° C. This mixture was allowed to stir for 30 minutes then a 4M solution of hydrogen chloride (4.48 ml, 17.90 mmol) in dioxane was added dropwise at approximately −10 to −15° C. The resulting slurry was then stirred for 10 minutes then filtered, washing with EtOH/Water (9:1, 100 mL), MeOH/EtOAc (1:1, 100 mL) and EtOAc (60 mL) and dried under vacuum (on rotavap) at 40° C. for 2 hours (constant weight) to afford 1,4-bis-{[2-(deuterated-d6-dimethylamino-N-oxide)ethyl]-amino)-5,8-di-hydroxyanthracene-9,10-dione (2.15 g, 3.99 mmol, 89% yield) as a dark blue powder.

The product was analysed by LCMS (standard 4 min. method, agilent), m/z 458.2 (M+H)⁺ (ES⁺), at 3.07 min, 98.3% purity @ 254 nm. ¹H NMR (400 MHz, D₂O) δ: 6.73 (2H, br s), 6.43 (2H, br s), 3.76 (4H, br s), 3.58 (4H, br s).

¹H NMR (D₂O) was consistent with the desired material.

Example B: In Vitro Properties of 1,4-bis-{[2-(deuterated-d6-dimethylamino-N-oxide)ethyl]amino)-5,8-di-hydroxyanthracene-9,10-dione and its Active Metabolite (a) The metabolites AQ4 and OCT1001 have similar cell cycle arresting actions, under normal oxygenation conditions, indicating that selective deuteration has not modified intrinsic biological activity.

A549 human lung cancer cells were cultured using conventional methods for adherent cells and exposed for 4 days to 0, 1, 3 or 10 nM agents under standard cell culture conditions of 5% carbon dioxide in air at 37 deg C. Harvested cells were permeabilised and stained with the DNA fluorescent dye ethidium bromide and cell cycle distributions determined by conventional flow cytometry.

FIG. 1 (flow cytometry) shows similar increases in the G2 peaks of the DNA content distributions between 3-10 nM (indicating cell cycle arrest) for cells exposed to exogenous metabolites 1,4-bis-{[2-(dimethylamino)ethyl]amino)-5,8-dihydroxy-anthracene-9,10-dione ("AQ4") and 1,4-bis-{[2-(deuterated-d6-dimethylamino)-ethyl]amino)-5,8-dihydroxy-anthracene-9,10-dione ("OCT1001").

(b) Similar hypoxia-enhanced cytotoxicity for AQ4N and OCT1002

Human T cell leukaemia cells (Jurkat) were cultured using conventional methods for suspension cultures in air or under 1% oxygen conditions for 4 days in the presence of a range of concentrations of either AQ4N or OCT1002. The relative cell number was determined using a conventional Coulter Counter particle counting method.

Figure 2:
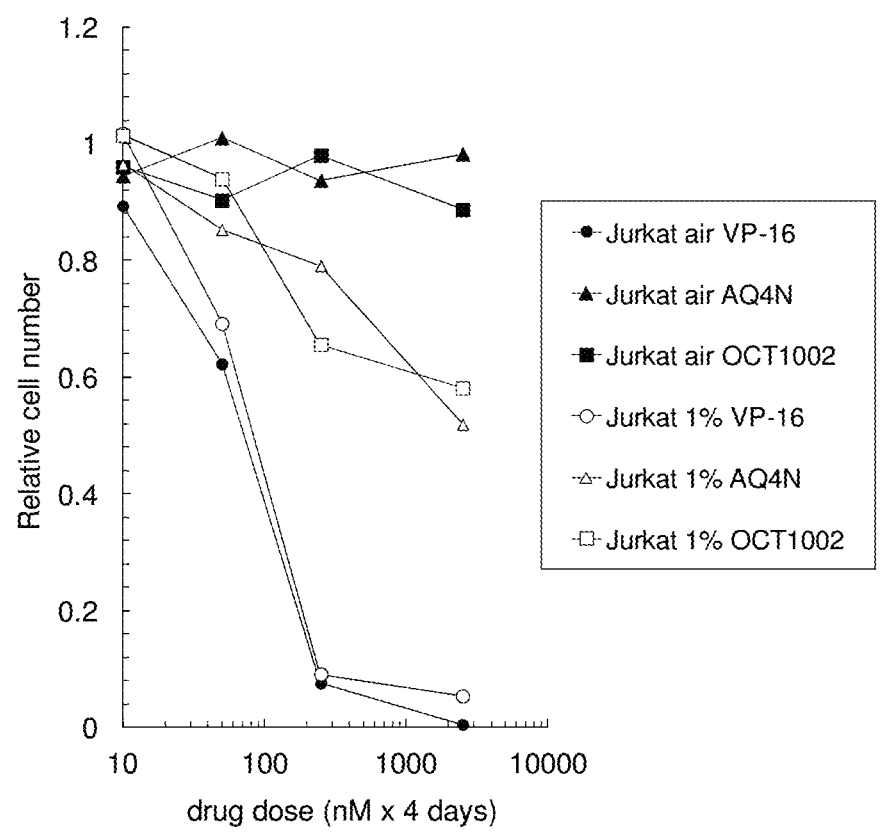
FIG. 2: Similar hypoxia-enhanced cytotoxicity for AQ4N and OCT1002
See Example B

FIG. 2 shows that the compounds tested require hypoxic conditions for the inhibition of cell proliferation. Thus, 1,4-bis-{[2-(dimethylamino-N-oxide)ethyl]amino)-5, 8-di-hydroxyanthracene-9,10-dione ("AQ4N") and 1,4-bis-{[2-(deuterated-d6-dimethyl-amino-N-oxide) ethyl]amino)-5,8-di-hydroxy-anthracene-9,10-dione ("OCT1002") both exhibit pronounced cytostatic activity under conditions of hypoxia (1% oxygen).

As a control it is shown that hypoxia does not modify the cytostatic action of a direct acting DNA topoisomerase inhibitor (VP-16), achieving similar levels of prolonged cytostatic action.

(c) Exemplification of that the bioactivity of AQ4N and OCT1002 is dependent upon the degree of hypoxia A549 human lung cancer cells were cultured using conventional methods for adherent cells and exposed for 4 days to varying concentrations of either AQ4N and OCT1002 agents under standard cell culture conditions of 5% carbon dioxide in air (normoxia) at 37 deg C., or under conditions of reduced oxygen (1% and 3%).

Data are plotted as relative population doublings determined by cell detachment and Coulter Counter particle counting of cell densities at the start and end of the exposure period.

Figure 3:
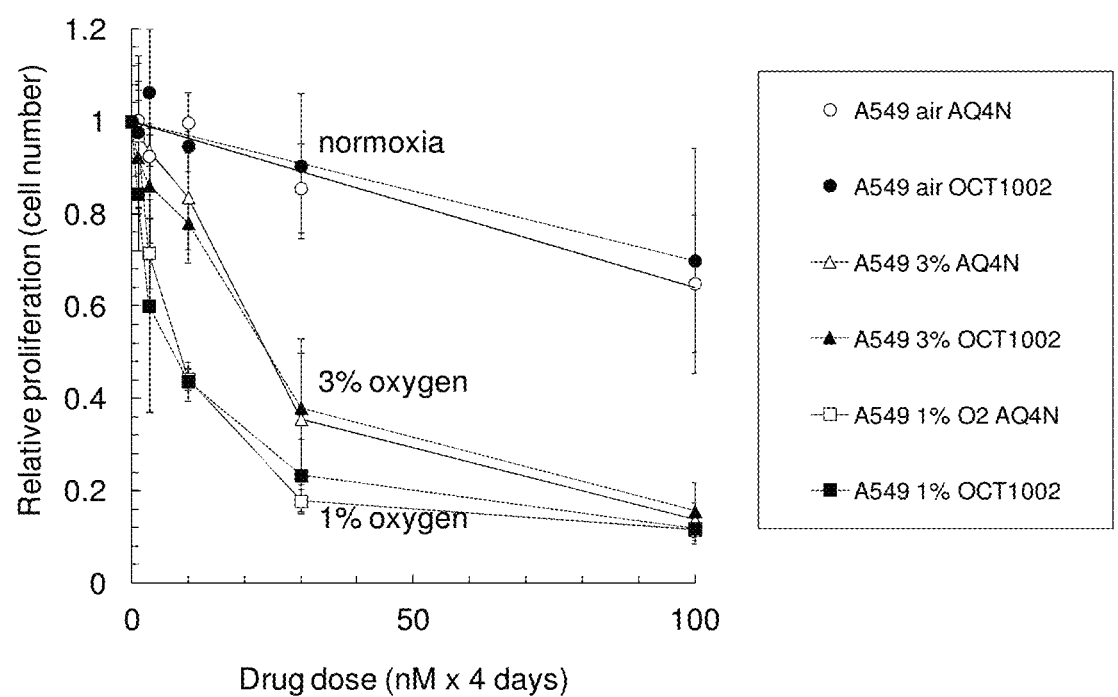
FIG. 3: Exemplification of that the bioactivity of AQ4N and OCT1002 is dependent upon the degree of hypoxia
See Example B

FIG. 3 shows that for the compounds tested, namely 1,4-bis-{[2-(dimethylamino-N-oxide)ethyl]amino)-5, 8-di-hydroxy-anthracene-9,10-dione ("AQ4N") and 1,4-bis-{[2-(deuterated-d6-dimethyl-amino-N-oxide) ethyl]amino)-5,8-di-hydroxyanthracene-9,10-dione ("OCT1002"), growth inhibition is dependent upon the degree of hypoxia and drug concentration, with the two agents showing similar responses.

(d) Hypoxic sensitisation by AQ4N and OCT1002

A549 human lung cancer cells were used in this experiment; culture conditions were as described in (c) above.

Cell cycle analysis was performed as described in (a) above.

Figure 4:
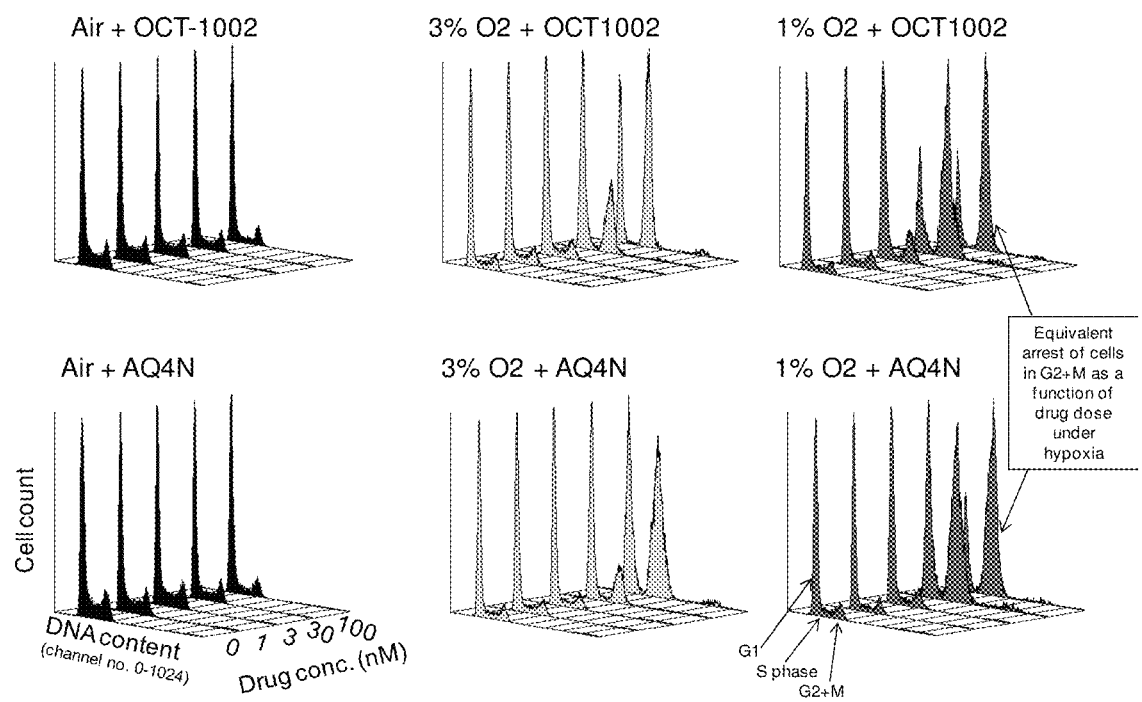
FIG. 4: Hypoxia-dependent growth inhibition by AQ4N and OCT1002 arises from a similar mechanism of cell cycle arrest and is dependent on the degree of hypoxia
See Example B FIGS. 5 (A & B): Exemplification of shared bioactivity of AQ4N and OCT1002 under hypoxic conditions for functional p53 (DoHH2) and mutant p53 (SU-DHL-4) human B cell lymphoma cells
See Example B

FIG. 4 shows that the compounds tested, namely 1,4-bis-{[2-(dimethylamino-N-oxide)ethyl]amino)-5,8-di-hydroxy-anthracene-9,10-dione ("AQ4N") and 1,4-bis-{[2-(deuterated-d6-dimethyl-amino-N-oxide)ethyl] amino)-5,8-di-hydroxy-anthracene-9,10-dione ("OCT1002"), generate similar cell cycle arrest (determined by flow cytometry) within the bioactive drug dose range.

The degree of late cell cycle arrest is increased as oxygenation levels are reduced.

(e) Exemplification of shared bioactivity of AQ4N and OCT1002 under hypoxic conditions for p53 functional and mutant p53 human B cell lymphoma cell lines Human B cell lymphoma cells were cultured using conventional methods for suspension cultures in air, 1% or 3% oxygenation conditions for 4 days in the presence of a range of concentrations of either AQ4N or OCT1002. The relative cell numbers were determined using a conventional Coulter Counter particle counting method.

Figure 5A:
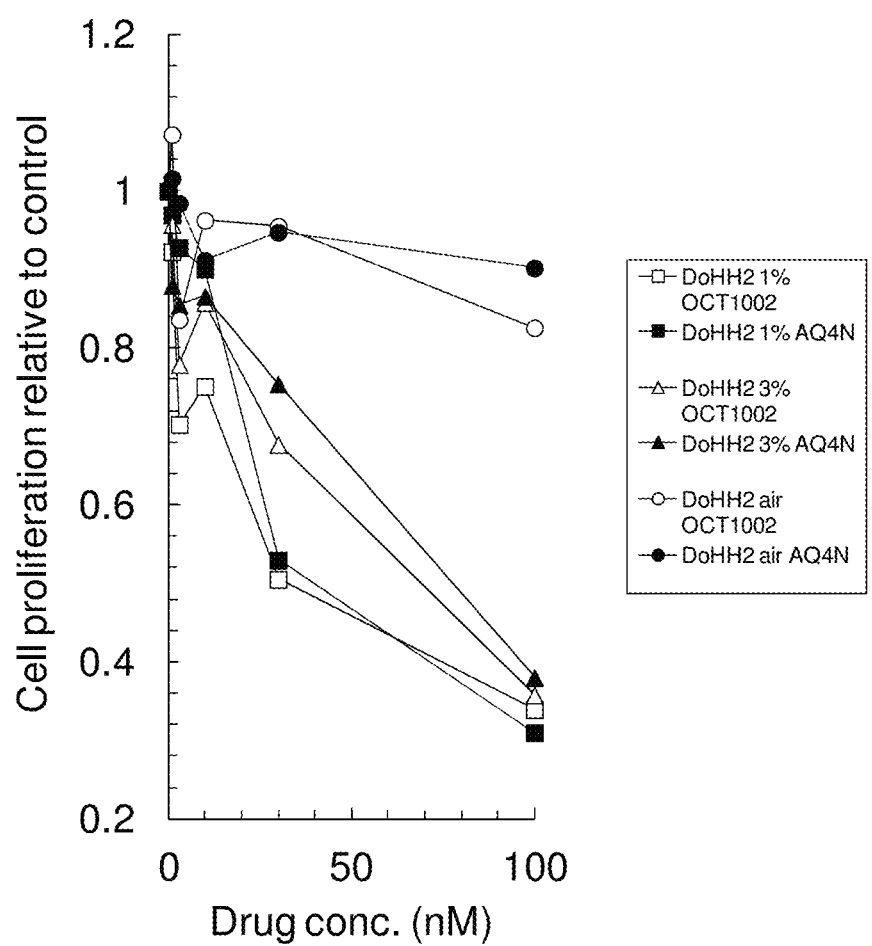

FIG. 5(A) shows that the compounds tested are equally and selectively cytotoxic in hypoxic conditions against DoHH2 human B cell lymphoma cells (bcl2 overexpressing; p53 wt) grown in suspension and exposed to prodrugs for 4 days under 21% (circles), 3% (triangles) or 1% $O_2$ (squares). Thus, 1,4-bis-{[2-(dimethylamino-N-oxide)ethyl]amino)-5,8-di-hydroxyanthracene-9,10-dione ("AQ4N") and 1,4-bis-{[2-(deuterated-d6-dimethyl-amino-N-oxide)ethyl]amino)-5,8-di-hydroxy-anthracene-9,10-dione ("OCT1002") both exhibit pronounced cytostatic activity under conditions of hypoxia (1% oxygen), with the growth inhibition being sensitive to the degree of hypoxia.

Figure 5B:
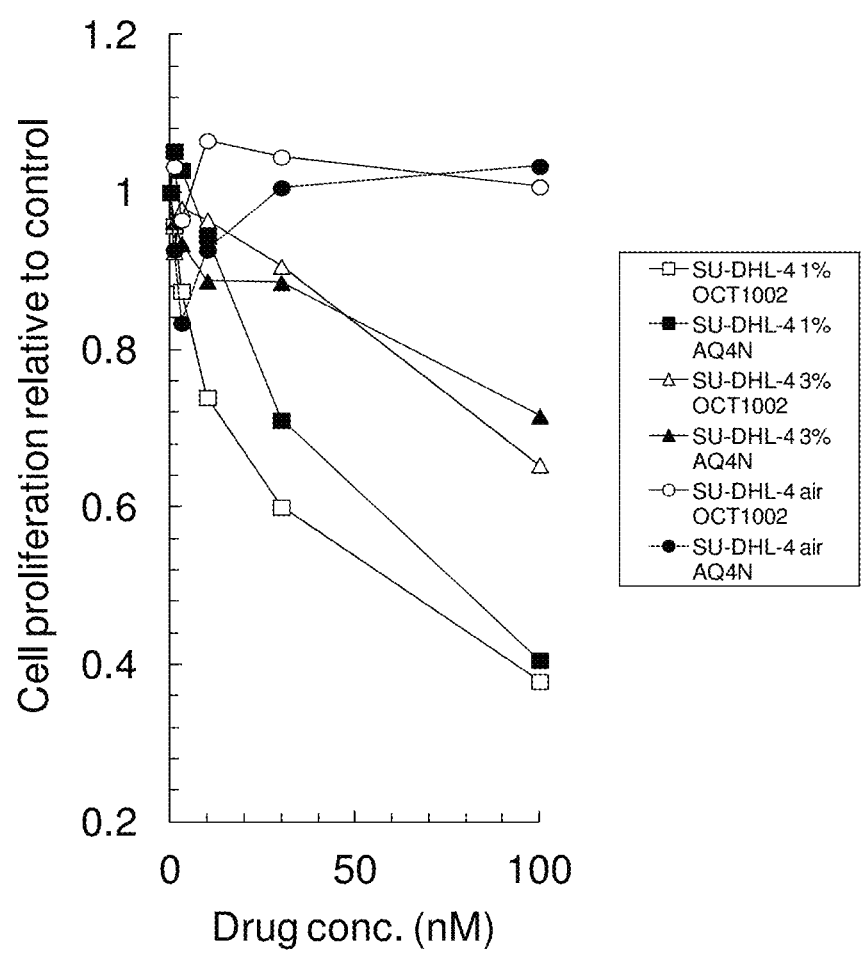

Likewise, FIG. 5(B) shows that the prodrugs AQ4N and OCT1002 are equally selectively cytotoxic in hypoxic conditions against SU-DHL-4 human B cell lymphoma cells (bcl2 overexpressing; p53 mutant) grown in suspension and exposed to prodrugs for 4 days under 21% (circles), 3% (triangles) or 1% $O_2$ (squares). Again, the growth inhibition is sensitive to the degree of hypoxia.

(f) Reciprocity between an imposed $pO_2$ level and the degree of end-product generation OCT1002 and AQ4N show reciprocity between an imposed $pO_2$ level and the degree of end-product generation in the biologically relevant range of hypoxia with low or undetectable levels of conversion under normoxia (and undetectable levels of AQ4N or OCT1002 showing that the metabolites are the primary persistent anthraquinone forms)

Relative to AQ4N, the deuterated variant OCT1002 shows a reduction in overall capacity for reduction/accumulation (HPLC analysis) within moribund cells, under protracted exposure conditions showing a reduction of 'redundant targeting' in a human lung cancer cell line. In this case redundant targeting of a prodrug refers to the over-generation of the cytotoxic form beyond that required for cell inactivation since conversion of the prodrug can continue even when cell cycle arrest has occurred. The consequences of over-generation will be increased deleterious effects of the converted form when released from the initial target cell. This undesirable bystander effect on nearby tissue not initially subject to hypoxic conditions will comprise non-target normal and tumour cells. Damage to normal cells is clearly undesirable. Suboptimal exposure of non-target tumour cells through a bystander effect may compromise their responses to other agent(s) delivered in combination or generate selective conditions for the development of drug resistance.

Table 1 shows a comparison of HPLC analysis of metabolite generation following exposure of human A549 cells to AQ4N and OCT1002 under varying degrees of hypoxia and concentration (data derived from two determinations) where 21% is taken to represent normal oxygenation conditions.

Data show the consistent reduction in the generation of OCT1001 compared with AQ4 in cells exposed to the conditions indicated and washed prior to assay for the presence of prodrug or their metabolites. Data also shows that the molecular forms present in cells experiencing hypoxia are the metabolites and not parent prodrugs.

TABLE 1

| Dose of prodrug (OCT1002 or AQ4N) nM × days | Humidified oxygenation conditions % $O_2$ | Humidified oxygenation conditions $pO_2$ mm Hg | pmoles metabolite generated per $10^5$ cells[a] AQ4 | pmoles metabolite generated per $10^5$ cells[a] OCT1001 | range AQ4 | range OCT1001 | Relative prodrug reduction to metabolite OCT1001/AQ4 |
|---|---|---|---|---|---|---|---|
| 30 | 1% | 7.1 | 9.25 | 5.64 | 1.46 | 1.20 | 0.61 |
| 30 | 3% | 21.4 | 0.78 | 0.49 | 0.05 | 0.06 | 0.62 |
| 30 | 21% | 142.2 | <0.10 | 0.10 | 0.03 | 0.02 | 1.02 |
| 100 | 1% | 7.1 | >42.95 | 16.17 | 6.59 | 8.16 | <0.38 |
| 100 | 3% | 21.4 | 5.58 | 1.93 | 1.13 | 0.16 | 0.35 |
| 100 | 21% | 142.2 | 0.23 | 0.11 | 0.08 | 0.03 | 0.50 |

[a]No AQ4N or OCT1002 detected in any sample indicating that either all prodrug forms are depleted by undergoing metabolism or that, by the method used, such forms are not readily retained within cells.

(g) Intracellular accumulation of the OCT001 far-red fluorescent chromophore under hypoxia is responsive to OCT1002 prodrug dose and oxygenation level Adherent A549 cells were cultured by conventional methods and exposed to 0, 30 or 100 nM OCT1002 for 4 days in air, 1% or 3% oxygenation levels. Detached cells were analysed far red fluorescence intensity using conventional flow cytometry and 633 nm wavelength excitation ($1 \times 10^4$ cells analysed).

Figure 6:
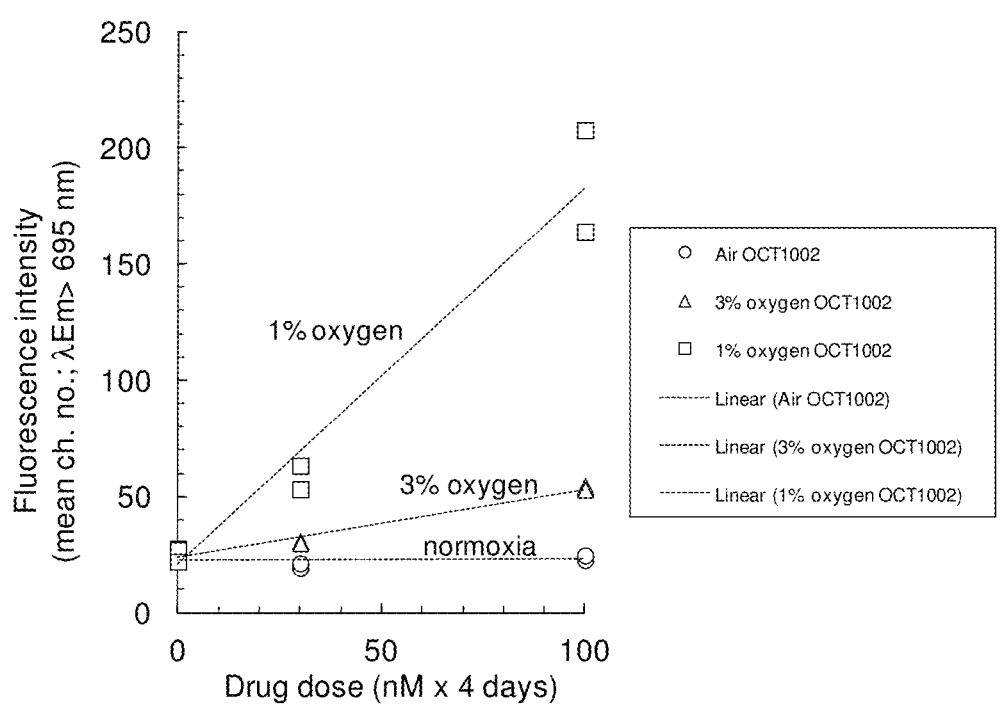
FIG. 6: Intracellular accumulation of the OCT1001 far-red fluorescent chromophore under hypoxia is responsive to OCT1002 pro-drug dose and oxygenation level
See Example B

FIG. 6 shows mean fluorescence intensity increases in a linear function of pro-drug dose and is dependent upon oxygenation levels. This provides a convenient fluorometric, single live cell analytical method for analyzing cell population experience of prevailing $pO_2$ levels.

(h) Deuteration does not affect the intrinsic capacity of the active metabolite (OCT1001) to accumulate A549 human lung cancer cells were used in this experiment, as described in (g) above.

Figure 7:
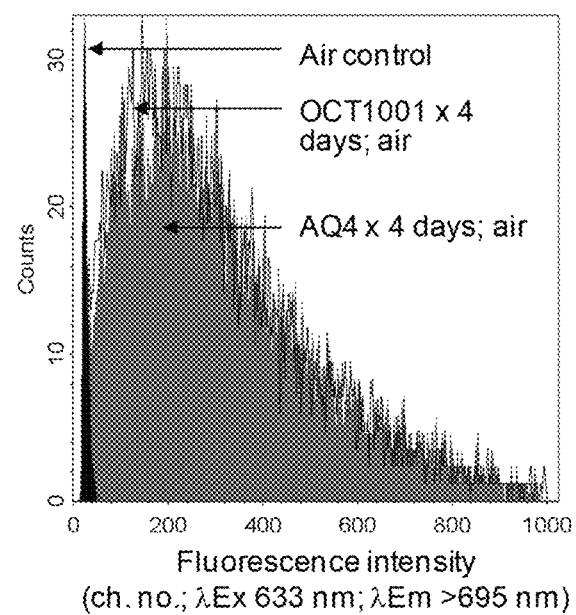
FIG. 7: Deuteration does not affect the intrinsic capacity of the metabolite (AQ4 or OCT1001) to accumulate within a cell
See Example B

Under normoxia conditions, similar levels of accumulation of OCT1001 and AQ4 were observed within cells (see FIG. 7). Thus, the overlaid histograms for the population distribution of fluorescence in cells exposed to AQ4 or OCT1001 under normoxia shows similar cellular accumulation potential.

(i) Accumulation of converted pro-drug OCT1001 correlates with growth arrest (increasingly moribund cells)

A549 human lung cancer cells were used in this experiment, as described in (g) above, with the exception that light side scatter (488 nm wavelength) was collected versus fluorescence intensity (>695 nm wavelength).

Figure 8:
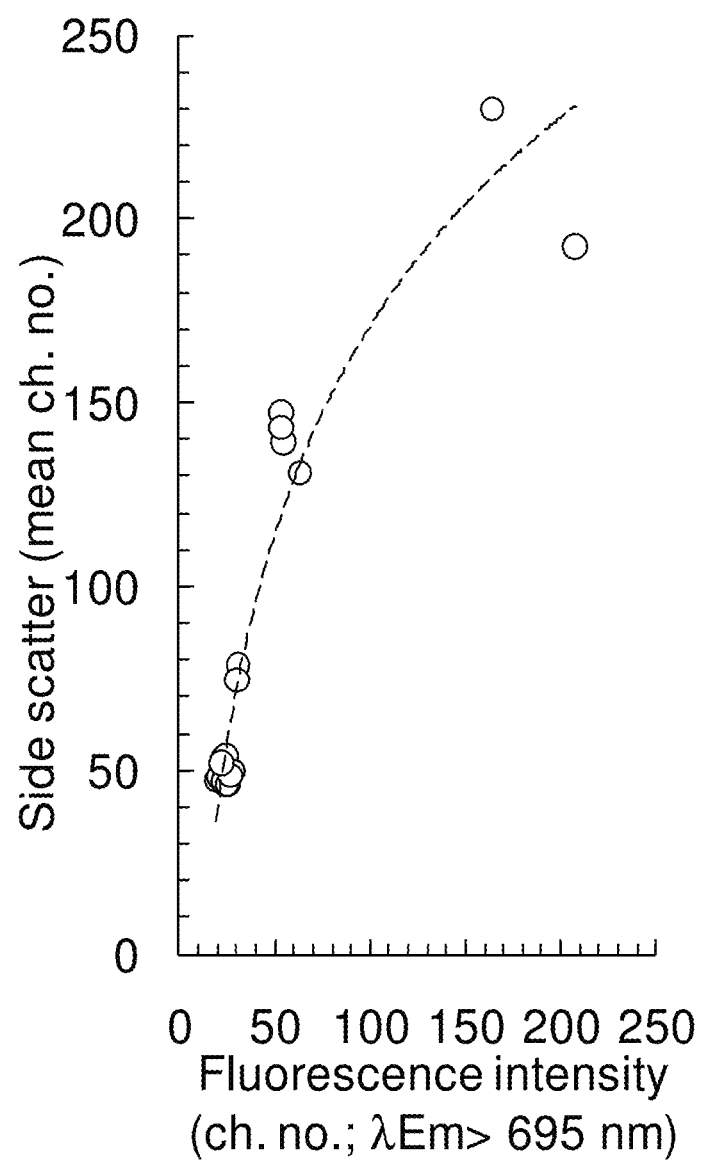
FIG. 8: Accumulation of converted pro-drug OCT1001 correlates with growth arrest
See Example B FIGS. 9 (A & B): Demonstration of intracellular fluorescence following exposure to OCT1002 under hypoxic conditions and that prodrug deuteration reduces intracellular accumulation but increases persistence of the metabolite.
See Example B

FIG. 8 shows collected flow cytometry data for A549 cells exposed to 0, 30 and 100 nM OCT1002 under 21%, 3% and 1% oxygen over 4 days.

Plotting all data points reveals that increasing light side scatter parameter (reflecting the expansion of cell size and complexity associated with growth arrest) correlates with the increase in fluorescence intensity (indicating co-accumulation of OCT1001).

(j) Demonstration of intracellular fluorescence following exposure to OCT1002 under hypoxic conditions and that prodrug deuteration reduces intracellular accumulation but increases persistence of the metabolite.

A549 cells were cultured using conventional methods and allowed to attach to the glass substrate in chamber slides and exposed to OCT1002 under hypoxia. Fluorescence imaging of live cells used conventional confocal fluorescence microscopy using red-line laser excitation.

Figure 9A:
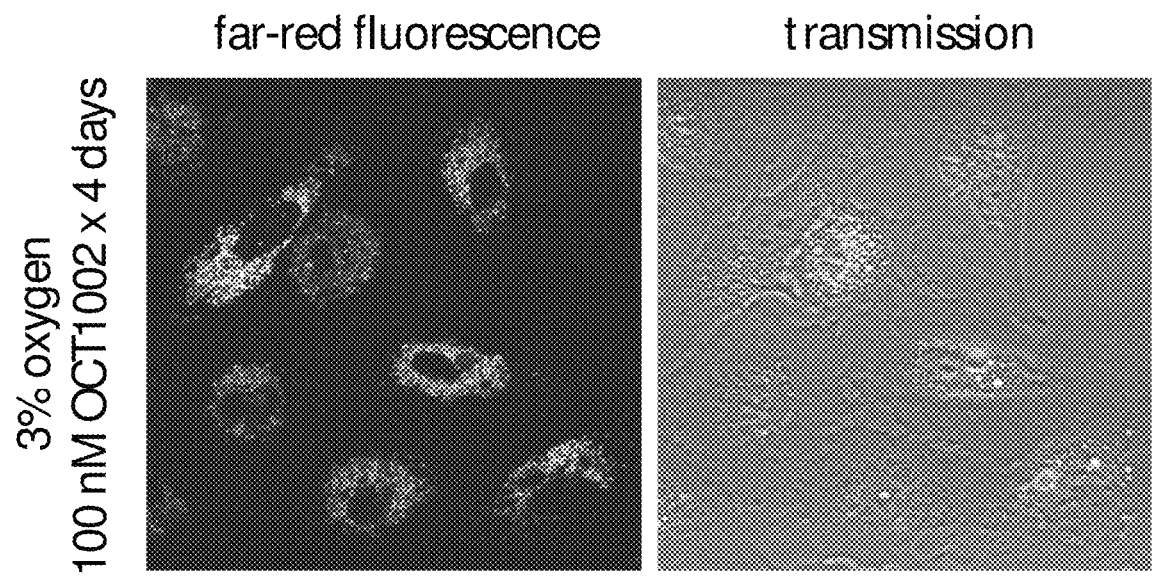

FIG. 9(A) shows that the far red fluorescence detected in cells is intracellular (background fluorescence not detectable in control cultures) with evidence of regions of cytoplasmic accumulation. The data exemplify the single cell hypoxia sensing properties of the deuterated pro-drug at the single-cell level.

Figure 9B:
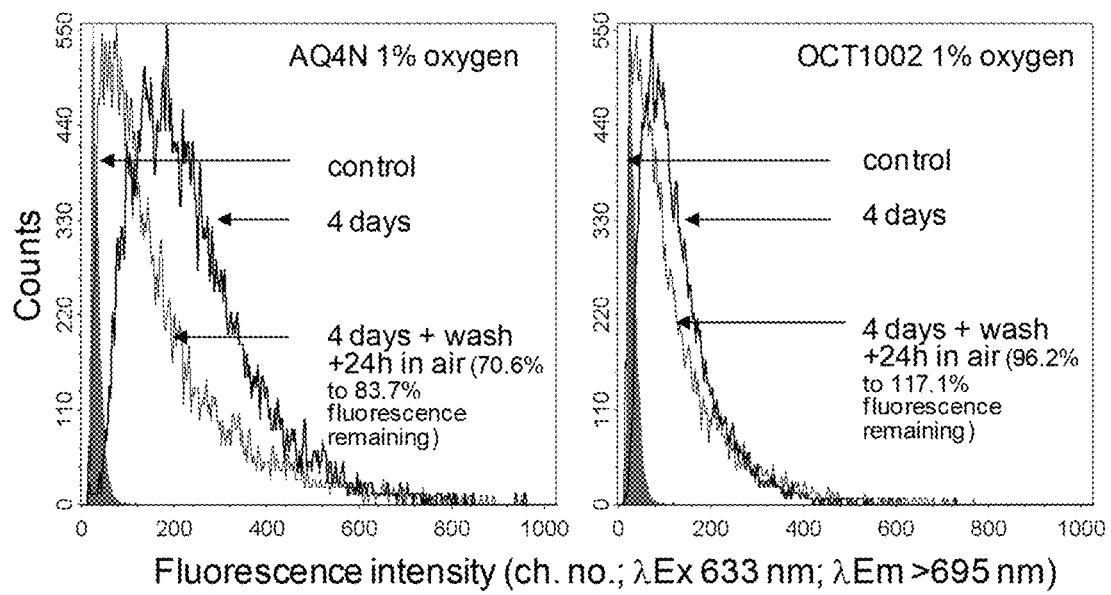

Given the confirmation of intracellular fluorescence associated with conversion of OCT1002 to OCT1001 under hypoxia, A549 human lung cancer cells were further used to assess differential accumulation or retention of the metabolites using flow cytometry as described in (g) above. Following exposure to AQ4N or OCT1002 under 1% oxygen, cells were detached for analysis, or washed and incubated for 24 h in drug free medium and held under normal oxygenation conditions prior to detachment and analysis by flow cytometry Flow cytometry data in FIG. 9(B) shows the reduced cellular accumulation (after 4 day exposure) but also reduced loss (after 24 h post exposure recovery) of intracellular fluorescence attributable to the metabolite OCT1001, compared with the fluorescence attributable to the metabolite AQ4, following exposure of A549 cells to pro-drugs OCT1001 and AQ4 in A549 under hypoxia. Thus, deuteration changes the in situ intracellular compartment loading/retention of hypoxia converted forms of OCT1002.

Conclusions

The above studies demonstrate the in vitro properties of an exemplary deuterated compound of the invention (the N-oxide prodrug, OCT1002, and its active metabolite, OCT1001).

(a) Evidence of primary biological activity following reduction of the prodrug in hypoxia that elicits growth arrest in different tumour cell types;

(b) For an equally effective toxicity for the reduced drug (OCT1001) the toxicity of OCT1002 to cells in normoxia is significantly less.

(c) Reciprocity between $pO_2$ level and end-product generation in the biologically relevant range of hypoxia;

(d) The ability of cellular fluorescence to report in situ generation of metabolite providing for the sensing and reporting of hypoxic environments;

(e) A distinct molecular/atomic signature provided by site-specific deuteration that can be used to trace prodrug conversion and metabolism by physico-chemical methods; and (f) Prodrug deuteration results in reduced accumulation of the reduced form under hypoxia but increased persistence/retention of the reduced form upon removal of external drug and re-oxygenation. This property demonstrated in moribund cells confirms both reduced redundant targeting of the deuterated form and convenient signal persistence for hypoxia sensing applications.

Example C—Effect of OCT1002 on Tumour Growth and Metastasis In Vivo

Given the hypoxia-activated cytotoxicity of the prodrug compounds of the invention, it may be advantageous to administer them as part of a combination treatment with one or more chemotherapeutic agents and/or radiotherapeutic modalities capable of decreasing (at least, transiently) tumour oxygenation levels in vivo. Bicalutamide (marketed as Casodex, Cosudex, Calutide, Kalumid) is an oral non-steroidal anti-androgen used in the treatment of prostate cancer including as monotherapy for the treatment of earlier stages of the disease. 22Rv1 is a human prostate carcinoma epithelial cell line (Sramkoski R M, Pretlow T G 2nd, Giaconia J M, Pretlow T P, Schwartz S, Sy M S, Marengo S R, Rhim J S, Zhang D, Jacobberger J W A new human prostate carcinoma cell line, 22Rv1. In Vitro Cell Dev Biol Anim. 1999 July-August; 35(7):403-9). The cell line expresses prostate specific antigen (PSA). Growth is weakly stimulated by dihydroxytestosterone and lysates are immunoreactive with androgen receptor antibody by Western blot analysis.

(i) Effect of Bicalutamide on the Oxygenation of 22Rv1 Prostate Tumours Grown as Xenografts Male SCID mice (>8 weeks) bearing 22Rv1 prostate tumours of 100-150 mm$^3$ were treated daily for 28 days by oral gavage with either vehicle (0.1% DMSO in corn oil) or bicalutamide (2 mg/kg/day in vehicle).

Before commencement of treatment (day 0) pO2 (mmHg) was measured using an Oxylite oxygen electrode probe; this was repeated on the days indicated.

Table 3 shows mean pO2 values ± SD.
Also shown are statistical comparisons of the bicalutamide group compared to control and to day 0 values; ns = not significant.

| Treatment | Day of Treatment | Mean pO2 ± SD (mmHg) | Significance (to vehicle) | Significance (to day 0) |
|---|---|---|---|---|
| Vehicle only | 0 | 15.277 ± 11.254 | | |
| | 7 | 14.741 ± 4.290 | | |
| | 14 | 3.165 ± 3.275 | | |
| | 21 | 2.660 ± 1.889 | | |
| | 28 | 3.546 ± 1.563 | | |
| Bicalutamide (2 mg/kg/day) | 0 | 15.277 ± 11.254 | ns | |
| | 7 | 1.996 ± 1.989 | <0.05 | <0.05 |
| | 14 | 0.486 ± 0.107 | ns | <0.05 |
| | 21 | 1.291 ± 0.291 | ns | <0.05 |
| | 28 | 11.905 ± 0.861 | <0.01 | ns |

22Rv1 cells grow as a solid tumour on the backs of SCID mice.

Tumour oxygenation was measured over 28 days in vehicle and bicalutamide (2 mg/kg/day) treated mice (see Table 3 above).

Figure 10:
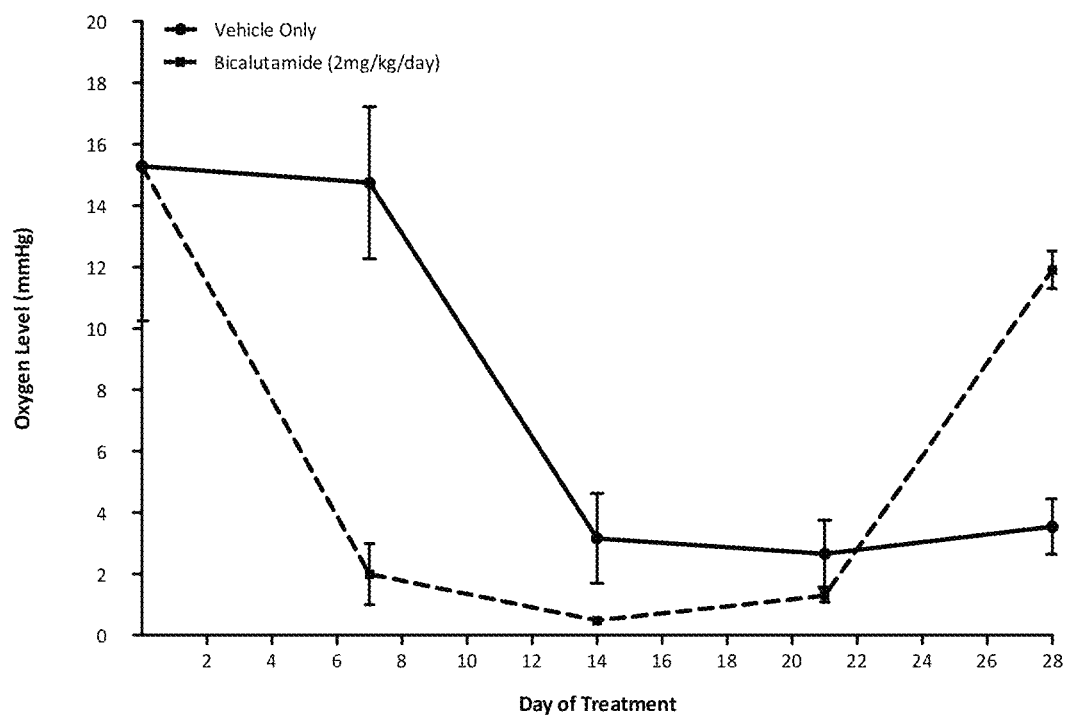
FIG. 10: Effect of bicalutamide on the oxygenation of 22Rv1 prostate tumours grown as xenografts
See Example C FIG. 11 (A-H): Effect of bicalutamide on blood vessels in 22Rv1 tumour xenografts. Tumour fragments were imaged before treatment began (A) vehicle and (E) bicalutamide pre-treatment groups and then after 7, 14 and 21 days of treatment, (B-D) vehicle only and (F-H) bicalutamide (10× magnification).
See Example C FIGS. 12 (A & B): Effect of bicalutamide only or AQ4N single dose or OCT1002 single dose on 22Rv1 xenografts in mice
See Example C FIGS. 13 (A & B): Combined effect of AQ4N single dose or OCT1002 single dose on 22Rv1 xenografts in mice treated daily with bicalutamide
See Example C

Bicalutamide caused a drop in tumour oxygenation (as shown in FIG. 10); from ~15.3 mmHg (2% oxygen) to 2.0 mmHg (0.3% oxygen) at day 7 and to 0.5 mmHg (0.1% oxygen) at day 14. This drop persists for approximately 2 weeks before recovering to almost normal somewhere beyond 21 and 28 (at which time it is not significantly different from the starting level of oxygenation).

The faster-growing, vehicle-treated, controls showed no significant drop in oxygen levels up to day 7. However, during the subsequent week (probably related to tumour size) the median oxygen levels drop to about 3 mmHg (0.4% oxygen) and do indicate recovery.

Conclusion

Hypoxia exists in the 22Rv1 solid tumour model. The addition of bicalutamide alters the patterns of oxygen levels indicated by the tumour. Hypoxia is clearly relevant to the 22Rv1 model and the response of such a model to monotherapy (±bicalutamide); and the potential role of OCT1002 in a combination treatment.

(ii) Effect of Bicalutamide on Blood Vessels in 22Rv1 Tumour Xenografts

Dorsal skin folds were secured using window chambers onto the backs of male SCID mice (>8 weeks). 22Rv1 tumour fragments were implanted and allowed to vascularise for 7 days before commencement of treatment.

Animals were treated daily via oral gavage with either vehicle (0.1% DMSO in corn oil) or bicalutamide (2 mg/kg in vehicle).

Anaesthetised mice were injected i.v. with FITC-labelled dextran immediately prior to imaging with a confocal microscope.

Each image is representative of a minimum of 5 animals per treatment group.

22Rv1 tumours were grown in window chambers/dorsal skin flaps on the backs of SCID mice. Tumour fragments were imaged (see FIG. 11) before treatment began (A) vehicle and (E) bicalutamide pre-treatment groups and then after 7, 14 and 21 days of treatment, (B-D) vehicle only (F-H) bicalutamide (10× magnification).

Within 7 days tumour fragments showed the development of extensive small vessels indicated as day 0 of the experimental period (see FIG. 11).

In vehicle-treated tumours vessel density showed a slight change by day 14 and by day 21 the small vessel numbers were reduced.

In bicalutamide-treated tumours, loss of small vessels was seen at days 7 and 14 with some recovery by day 21. This is consistent with oxygen electrode data i.e., fall and then recovery of oxygenation.

Conclusions

Vehicle has no effect on blood vessels for at least 7 days. By day 14 there is a slight pruning of vessels which is clearly seen by day 21. This vessel loss, although not as dramatic as seen in the bicalutamide treated tumours (at days 7 and 14; Ming et al., 2007), may be due to vascular collapse and necrosis seen at this time in this fast growing vehicle-treated tumour. The oxygen levels drop somewhat earlier, i.e. sometime between days 7 and 14 (see FIG. 10).

In bicalutamide-treated 22Rv1 tumours there is a marked early loss of tumour vasculature (by day 7). The data provide evidence that bicalutamide causes a profound drop in tumour oxygenation through an anti-vascular effect; this may be direct or alternatively it could be due to inhibition of the production of pro-angiogenic factors by the tumour cells.

By day 21, the small vessels have returned which is consistent with the increased level of oxygenation seen in FIG. 10.

(iii) Effect of Bicalutamide Only or AQ4N Single Dose or OCT1002 Single Dose on 22Rv1 Xenografts in Mice.

Male SCID mice (>8 weeks) bearing 22Rv1 xenograft tumours of 100-150 mm3 were treated for 28 days.

Treatment included Vehicle (0.1% DMSO in corn oil) or bicalutamide (2 mg/kg/day in vehicle) both administered daily via oral gavage. Alternatively, at day 7 of the experimental period AQ4N or OCT1002 (50 mg/kg in sterile PBS) was administered intraperitoneally as a single dose.

Tumour volumes were measured using callipers every other day.

Data analysis to determine the time dependent effect of treatment(s) on tumour volume was performed. Tumour volume was normalised to day 6 (ie pre-prodrug addition). Time series and regression analysis was undertaken.

Figure 12A:
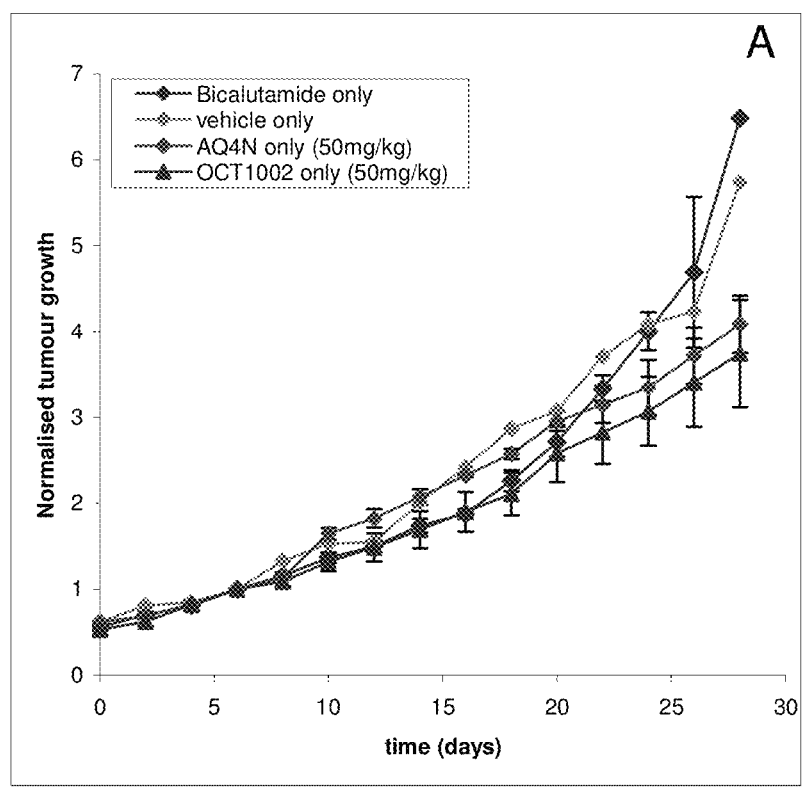

Tumour growth is normalised to day 6, so that overall tumour growth, and patterns can be compared FIGS. 12 (A and B).

Despite the lack of sensitivity to bicalutamide in vitro, the 22Rv1 tumours show a small but significant slowing of growth. Classical cross-sectional comparison of growth delay showed that mice treated with vehicle required 14.0±0.3 days to reach four times the volume at the start of treatment. Bicalutamide treatment (2 mg/kg/day) increased this to 18.5±0.8 days; thus this was a growth delay of 4.5 days.

Graphical regression fits indicate that 22RV1 tumours treated with bicalutamide only show a delay in growth (during days 10-20), despite continuing daily exposure to bicalutamide; the tumours exhibit an overall exponential growth pattern ($R^2=0.9915$) to day 24.

Addition of AQ4N given as a single dose (50 mg/kg) on day 7, a different growth pattern was observed compared to that of the bicalutamide treatment alone, regression fitting showed a non-linear polynomial growth pattern ($R^2=0.9948$).

Addition of OCT1002 given as a single dose (50 mg/kg) on day 7; tumours treated with this single dose were capable of maintaining a polynomial ($x^2$) growth rate pattern, this was also a non-linear pattern ($R^2=0.9978$).

Figure 12B:
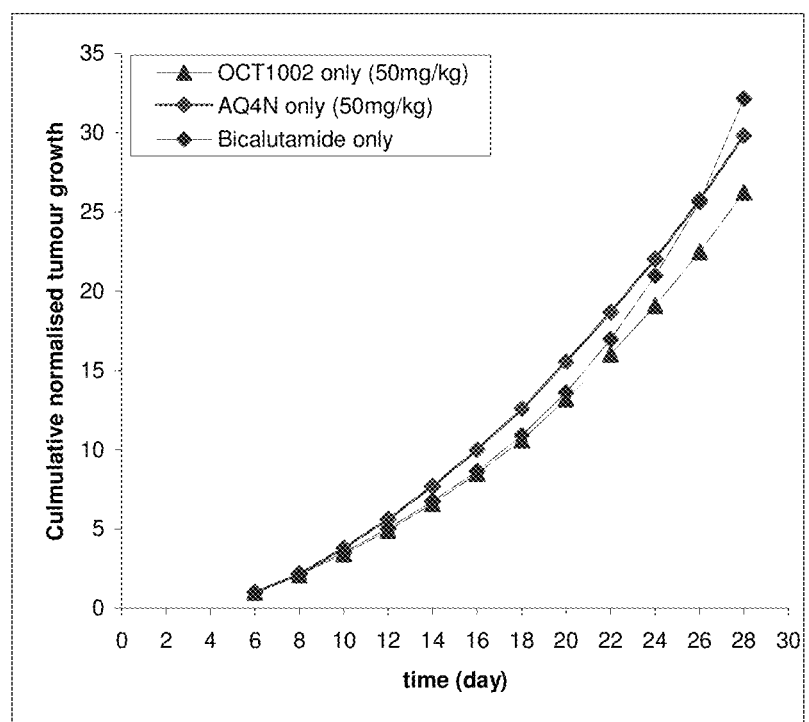

OCT1002 treated tumours showed an overall reduced rate of growth over the remaining period of the experiment (beyond day 22) compared to the bicalutamide only and AQ4N only treated tumours. Cumulative growth over the entire period (progressive area under the curve), indicates this difference (FIG. 12B).

(iv) Combined Effect of AQ4N Single Dose or OCT1002 Single Dose on 22Rv1 Xenografts in Mice Treated Daily with Bicalutamide Male SCID mice (>8 weeks) bearing 22Rv1 xenograft tumours of 100-150 mm³ were treated for 28 days. Vehicle (0.1% DMSO in corn oil) and bicalutamide (2 mg/kg/day in vehicle) treatments were administered daily via oral gavage.

AQ4N or OCT1002 (50 mg/kg in sterile PBS) was administered intraperitoneally as a single dose at day 7.

Tumour volumes were measured using callipers every other day.

Animals were culled once the tumour burden reached ≥800 mm³.

Figure 13A:
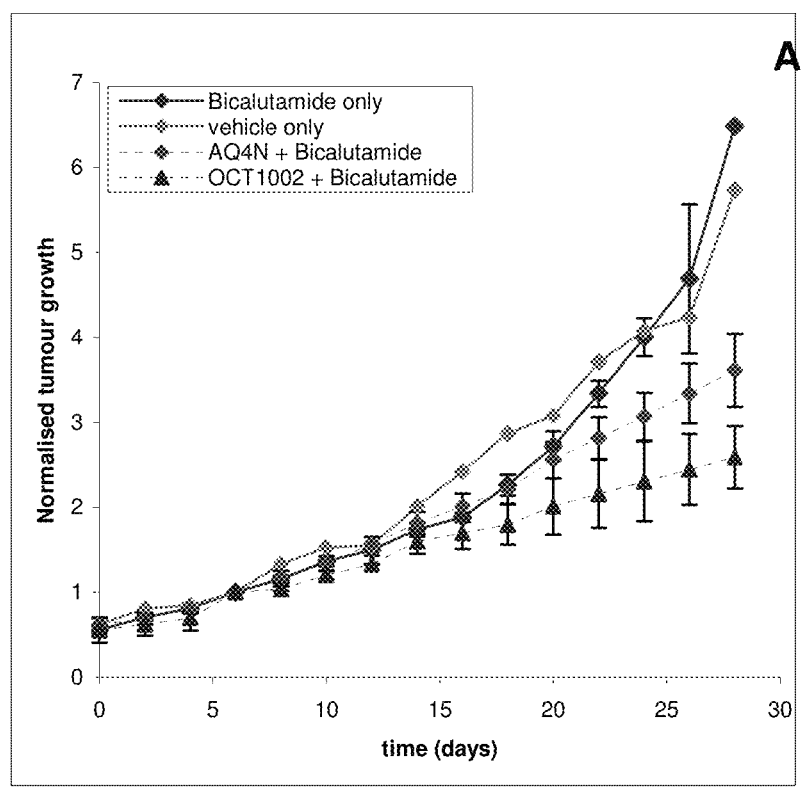
Figure 13B:
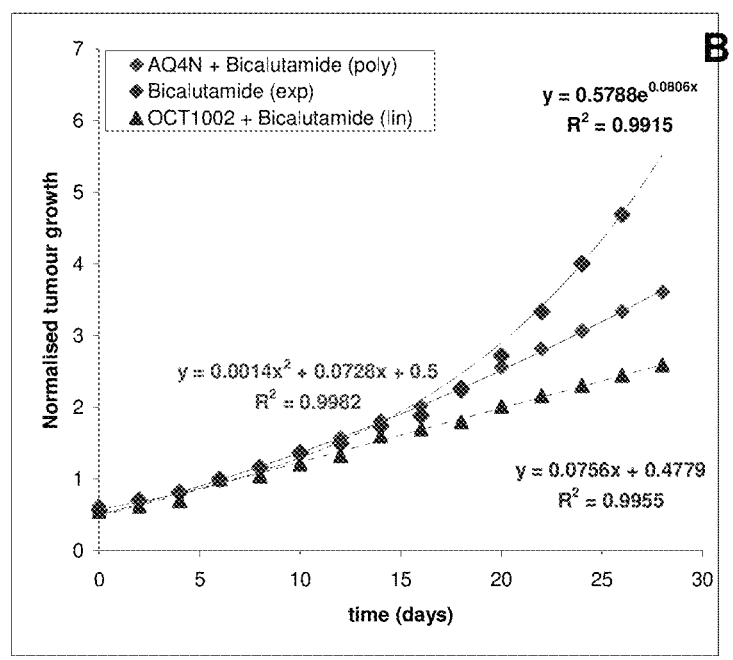
Figure 14:
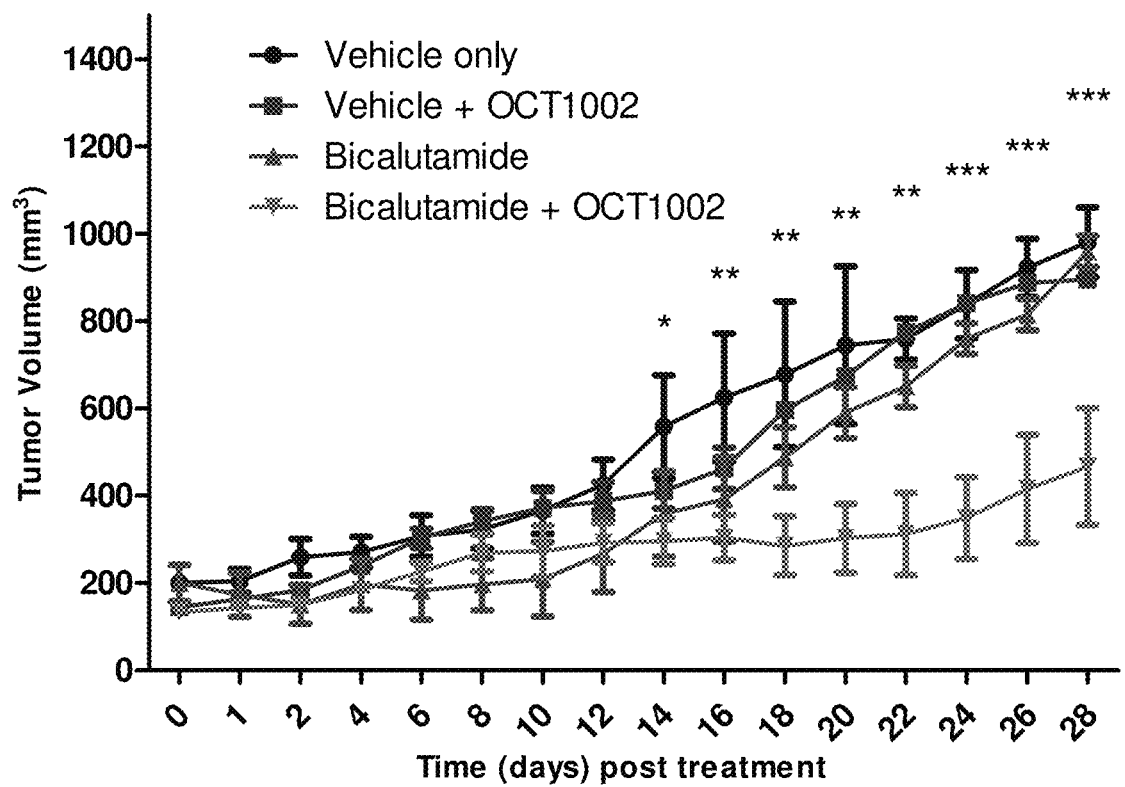
FIG. 14: Effect of OCT1002 on LNCaP xenografts in mice treated with/without bicalutamide
See Example C FIG. 15 (A-C): OCT1002 is reduced in hypoxic LNCaP tumour cells in vivo In mice treated with vehicle+OCT1002 at day 7: the converted compound OCT1001 (blue) is in a few areas where vascularisation is poor (FIG. 15A). Mice treated with bicalutamide (2 mg/kg/day in vehicle): vascularisation was reduced at days 7. On day 7, two hours after intraperitoneal injection of a single dose of OCT1002 (50 mg/kg) large quantities of converted compound (OCT1001; blue) can be seen across the whole tumour fragment (FIG. 15B). OCT1001 (blue) is still localised to the tumour at day 14; by day 21 the amount of compound was considerably lower (FIG. 15C).
See Example C

Tumour growth is normalised to day 6, so that overall tumour growth, and patterns can be compared (FIGS. 13 (A and B)).

Bicalutamide treatment alone (2 mg/kg/day) is discussed above; it exhibits a overall exponential growth pattern ($R^2=0.9915$) to day 24.

Bicalutamide treatment was combined with an AQ4N single dose (50 mg/kg) given on day 7, a modified growth pattern was observed compared to that of the bicalutamide treatment alone, regression fitting showed a non-linear polynomial growth pattern ($R^2=0.9982$), with divergence of growth to bicalutamide alone apparent at beyond day 20.

Bicalutamide treatment treatment was combined with an OCT1002 single dose (50 mg/kg) given on day 7; a different modified growth pattern was observed regression fitting showed a linear tumour growth response ($R^2=0.9955$), with divergence of growth to bicalutamide alone apparent at beyond day 14.

Conclusions

The combined treatment indicates two critical features.
(i) the first is an earlier effective tumour growth inhibition of OCT1002 on the bicalutamide treated tumours compared to AQ4N;
(ii) the second indicates a sustained tumour growth inhibition (indicated by a maintained linear response); that reflects a persistence OCT1002 and tumour growth inhibition.

Thus with OCT1002 administered at the time when hypoxia/low oxygen levels were achieved; an early and sustained effect was obtained. The combination of OCT1002 with bicalutamide was more effective at inhibiting tumour growth as compared to AQ4N with bicalutamide.

(v) Effect of OCT1002 on LNCaP Xenografts in Mice Treated with/without Bicalutamide Male SCID mice (>8 weeks) bearing LNCaP xenograft tumours of 100-150 mm³ were treated for 28 days.

Vehicle (0.1% DMSO in corn oil) and bicalutamide (2 mg/kg/day in vehicle) treatments were administered daily via oral gavage. OCT1002 (50 mg/kg in sterile PBS) was administered intraperitoneally as a single dose at day 7.

Tumour volumes were measured using callipers every other day.

Growth curves are the mean of ≥5 animals in bicalutamide and vehicle treatment groups; bicalutamide+OCT1002 group (n=5 until day 14; then n=3) and vehicle+OCT1002 (n=5 until day 13; n=1)±s.e.

Table 6 below shows the growth delays calculated for the time to reach twice the treatment size.

Bicalutamide causes a 5.1 day delay in LNCaP tumour growth compared to vehicle.

When OCT1002 (50 mg/kg single dose on day 7) was given in combination with vehicle (daily administration) there was no appreciable effect on tumour growth (Table 6 below).

Bicalutamide (daily for 28 days) initially slows tumour growth until day 12-14. Tumour growth then recovers and the tumours are the same size as the vehicle-treated tumours by day 28 (Table 6 below).

Tumours treated with a single dose of OCT1002 reduced the growth rate in combination with bicalutamide and this was significantly different from control at all times between days 14 and days 28 at the termination of the experiment (FIG. 15).

Conclusions

Administration of OCT1002 at day 7 had no significant effect on LNCaP tumour growth. This shows that the better-oxygenated tumours (i.e. as compared to bicalutamide-treated tumours) there is low toxicity of OCT1002 and that this better-oxygenated fraction of cells is predominant in contributing to growth in vehicle-treated control tumours.

Combination of a single dose of OCT1002 with bicalutamide blocked the increase in growth rate observed in the bicalutamide-treated group. OCT1002 is very effective at blocking tumour growth from 12 days onwards where, for bicalutamide alone, there is a delay and then recovery.

The initial slowing and then recovery after day 14 of LNCaP tumour growth, during daily treatment with bicalutamide, is consistent with the drop and then recovery of tumour oxygenation and blood vessels (Ming et al., 2012, supra.).

TABLE 6

| Treatment | Time to 2x start volume (days) | Growth Delay (days) |
|---|---|---|
| Vehicle Only | 11.2 ± 1.88 | |
| Bicalutamide | 16.2 ± 1.94 | 5 ± 3.82 |
| OCT1002 only | 13 ± 0.89 | 1.8 ± 2.77 |
| OCT1002 + Bicalutamide | 25.5 ± 3.22 | 14.3 ± 5.1 |

(vi) OCT1002 Prodrug is Converted to Metabolites in Hypoxic LNCaP Tumour Cells In Vivo Methods A dorsal skin flap (window chamber) was attached to the dorsum of male SCID mice and a 1 mm$^3$ LNCaP-Luc tumour fragment inserted; this was left to vascularise for 7 days.

Mice were then treated orally for 21 days with either vehicle (0.1% DMSO in corn oil) or bicalutamide (2 mg/kg/day).

Seven days after induction of (a) vehicle or (b) bicalutamide mice were dosed intraperitoneally with OCT1002 (50 mg/kg).

Two hours after injection of OCT1002 mice were injected intravenously with FITC-dextran.

Images were captured using a confocal laser scanning microscopy to show blood vessels (green) and OCT1001 (blue) patterns in the tumour. (Magnification 10× with 3× digital zoom) (pixel resolution).

Images were also acquired at day 0 (i.e. 7 days after tumour fragment implantation), 14 and 21.

Only FITC-dextran was administered on days 0, 14 and 21. (c) Full panel of images 0, 7, 14 and 21 days.

Control mice were treated orally for 21 days with vehicle (0.1% DMSO in corn oil): vascularisation was maintained throughout. By 7 days the tumour fragment was vascularised (day 0 of experiment shown in FIG. 15C green).

Figure 15A:
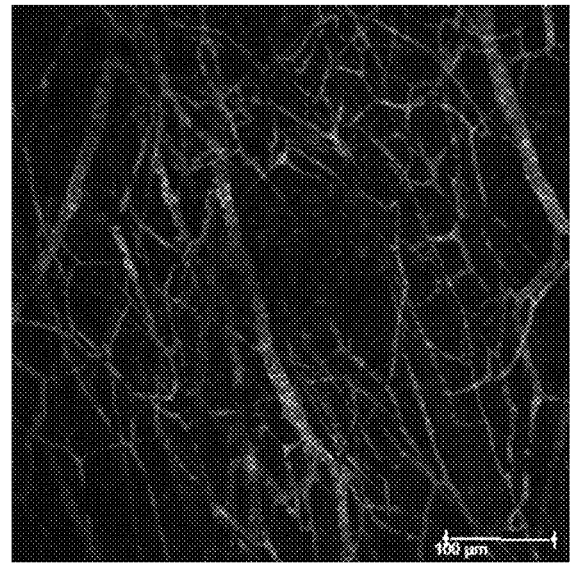

In mice treated with vehicle+OCT1002 at day 7: the converted compound OCT1001 (blue) is in a few areas where vascularisation is poor (FIG. 15A).

Figure 15B:
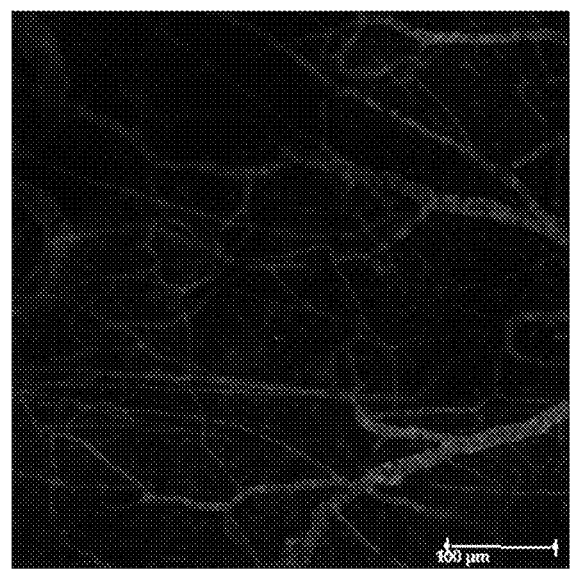

Mice treated with bicalutamide (2 mg/kg/day in vehicle): vascularisation was reduced at days 7. On day 7, two hours after intraperitoneal injection of a single dose of OCT1002 (50 mg/kg) large quantities of converted compound (OCT1001; blue) can be seen across the whole tumour fragment (FIG. 15B).

Mice treated with bicalutamide (2 mg/kg/day in vehicle): vascularisation was reduced at days 7 and 14, this recovered by day 21 (Ming et al., 2012, supra.).

Tumours were re-examined at days 14 and 21.

Figure 15C:
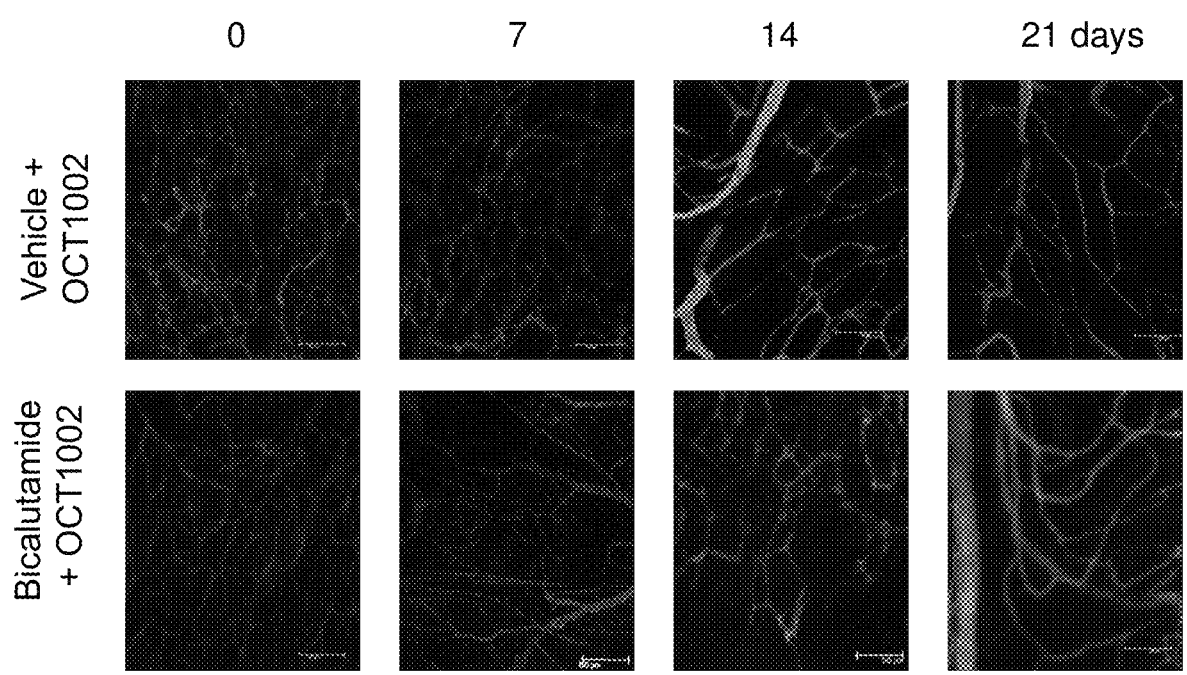

OCT 1001 (blue) is still localised to the tumour at day 14; by day 21 the amount of compound was considerably lower (FIG. 15C).

Conclusions

OCT1002, administered intraperitoneally, distributed widely throughout the tumour fragments localised in the skin fold on the backs of the mice.

Distribution was extensive even when the vasculature was significantly decreased (i.e. by the bicalutamide treatment at days 7 and 14).

OCT1001 was found predominantly where the oxygen levels are low (i.e. areas of poor vascularisation); small areas were seen in the control also (indicating that hypoxia can occur in untreated tumours but to a lesser extent.

Extensive localisation of OCT1001 was still observed at day 14 of bicalutamide treatment showing that the compound remains for at least 7 days.

By day 21, tumour blood vessels show some recovery and OCT1001 levels are lower although still above background.

The persistence of the reduced product, OCT1001, for >7 days shows that the half-life of the converted compound is long.

However it may be less than AQ4 since by day 21 the OCT1001 signal is very much decreased.

This may be due to the different cellular binding properties of OCT1001 as compared to AQ4 and potentially will provide a rationale for less cumulative systemic toxicity which might be caused through persistence of small amount of reduced compound in marginally hypoxic peripheral tissues. This should not affect the primary efficacy of OCT1002/OCT1001 at the predominant site of metabolism (i.e. the hypoxic cells in tumours) since large amounts are seen throughout the hypoxic tumour fragment which persists for greater than 7 days.

(vii) OCT1002 Reduces the Metastatic Spread of LNCaP Tumours to the Lungs

Methods

Male SCID mice (>8 weeks) bearing LNCaP-luc xenograft tumours of 100-150 mm$^3$ were treated for 28 days (the luciferase-expressing cells had similar characteristics to parental LNCaP cells; Ming et al., 2012, supra.).

Vehicle (0.1% DMSO in corn oil) and bicalutamide (2 mg/kg/day in vehicle) treatments were administered daily via oral gavage.

OCT1002 (50 mg/kg in sterile PBS) was administered intraperitoneally as a single dose at day 7.

On day 28 of treatment, animals were injected i.p. with a solution of D-luciferin (150 mg/kg in PBS) 15 mins prior to imaging.

Animals were then killed and a range of tissues were removed for the detection of bioluminescence using the IVIS imaging system (Xenogen, USA).

Images were taken for 5 minutes and quantification of bioluminescence was achieved by drawing a region of interest around the area and measuring total flux in photons/second (ph/sec).

Figure 16:
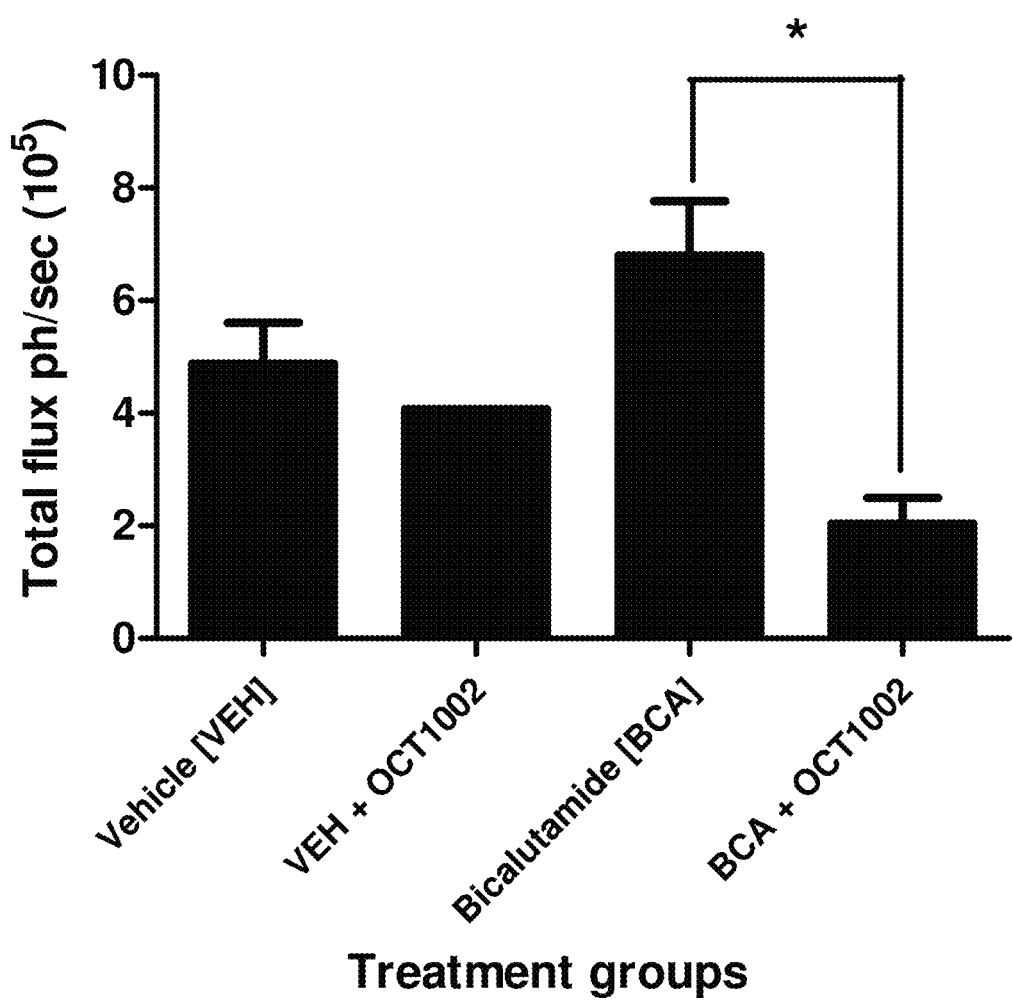
FIG. 16: OCT1002 reduces the metastatic spread of LNCaP tumours to the lungs
See Example C

A range of tissues were excised, however only the lungs and tumour showed measurable bioluminescence. The mean±s.e of bioluminescence in the lungs is shown in FIG. 16; bicalutamide and vehicle treatment groups (n=10); bicalutamide+OCT1002 group (n=3). and vehicle+OCT1002 (n=1). * Bicalutamide vs bicalutamide+OCT1002 (p=0.024). Mice treated with vehicle showed some metastatic spread to the lung. OCT1002, single dose day 7, had no effect on this spread.

Bicalutamide appeared to increase the extent of metastatic spread although the result did not reach significance.

Combination of OCT1002 with bicalutamide showed that OCT1002 significantly reduces the metastatic spread to the lungs caused by bicalutamide. (P=0.024)

Conclusions

OCT1002 given as a single dose at day 7 was able to reduce significantly the metastatic spread to the lungs caused by bicalutamide treatment.

The invention claimed is:

1. A compound of Formula IV or VI:

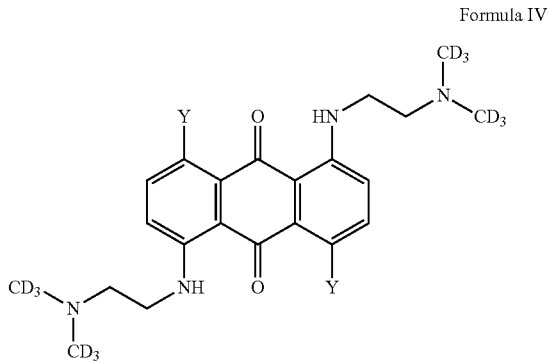

wherein Y are each independently selected from the group consisting of hydrogen, hydroxy, halogeno, amino, $C_{1-4}$ alkoxy and $C_{2-8}$ alkanoxy.

2. A compound according to claim 1, wherein the compound is of Formula VIII or X:

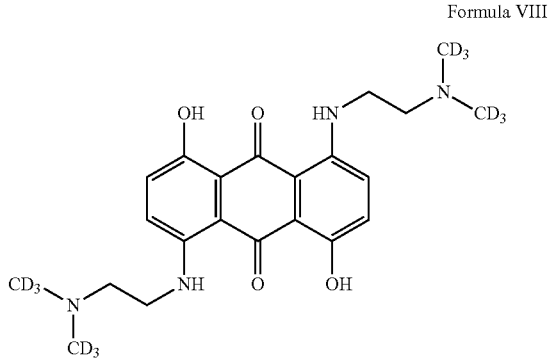

3. A compound according to claim 1 wherein the compound is in the form of a halide salt, for example a chloride salt.

4. The compound according to claim 1 wherein each Y is independently selected from the group consisting of hydrogen, hydroxy and halogeno.

5. A pharmaceutical composition comprising a compound according to claim 1 together with pharmaceutically acceptable buffer, diluent, carrier, adjuvant or excipient.

6. A pharmaceutical composition according to claim 5 formulated for parenteral administration.

7. A kit for detecting the oxygenation level of cells comprising a compound according to claim 1.

8. A kit according to claim 7 further comprising a non-deuterated form of a compound of Formula VI.

9. A process for making a compound according to claim 1 comprising reacting an anthracene-9,10-dione with a deuterated alkylenediamine under conditions suitable for the production of an alkylaminoalkyl-aminoanthraquinone.

10. A process according to claim 9 further comprising the step of reacting the alkylaminoalkylaminoanthraquinone with a monoperoxyphthalate to under conditions suitable for the production of an N-oxide derivative of the alkylamino-alkylaminoanthraquinone.

11. A process according to claim 9 comprising reacting 1,4-difluoro-5,8-dihydroxyanthracene-9,10-dione, 281-005 with deuterated--N,N-dimethylethylene-diamine under conditions suitable for the production of 1,4-bis-{[2-(deuterated-d6-dimethylamino)ethyl]amino)-5,8-dihydroxyanthracene-9,10-dione.

12. A process according to claim 11 further comprising the step of reacting the 1,4-bis-{[2-(deuterated-d6-dimethylamino)ethyl]amino)-5,8-dihydroxyanthracene-9,10-dione with magnesium monoperoxyphthalate under conditions suitable for the production of 1,4-bis-{[2-(deuterated-d6-dimethylamino-N-oxide)ethyl]amino)-5,8-dihydroxy-anthracene-9,10-dione.

13. A method of treating cancer in a patient comprising administering to the patient a therapeutically effective amount of the compound according to claim 1, wherein the cancer is pancreatic cancer, prostate cancer, or both.

14. A method according to claim 13 wherein the patient is human.

15. A method according to claim 13, wherein administering the therapeutically effective amount treats metastases or reduces metastatic spread.

16. A method according to claim 13 wherein the compound is a monotherapy.

17. A method according to claim 13 further comprising administering to the patient one or more additional cancer treatments.

18. A method according to claim 17 wherein the one or more additional cancer treatments is/are selected from the group consisting of anti-androgens (steroidal and non-steroidal), vascular disrupting agents, anti-angiogenic agents, anti-VEGFR agents, IL8 inhibitors, NO synthase inhibitors, vasoconstricting agents, vasodilating agents, and radiotherapeutic modalities.

19. A method according to claim 18 wherein the one or more additional cancer treatments is at least one anti-androgen.

20. A method according to claim 19 wherein the at least one anti-androgen is selected from the group consisting of flutamide, nilutamide, bicalutamide, finasteride, dutasteride, bexlosteride, izonsteride, turosteride, epristeride and abiraterone.

21. A method according to claim 20 wherein the at least one anti-androgen is bicalutamide.

22. The method according to claim 17 wherein the one or more additional cancer treatments decreases tumour oxygenation in vivo.

23. The method according to claim 22 wherein the one or more additional cancer treatments lowers the median oxygen level of the tumour to below 3%.

24. The method of treating cancer in the patient according to claim 13, wherein the cancer is pancreatic cancer.

25. The method of treating cancer in the patient according to claim 13, wherein the cancer is prostate cancer.

26. The method according to claim 25, wherein administering the therapeutically effective amount treats metastases or reduces metastatic spread.

27. The method according to claim 25 further comprising administering to the patient one or more additional cancer treatments in combination with the therapeutically effective amount of the compound.

28. The method according to claim 27 wherein the one or more additional cancer treatments is/are selected from the group consisting of anti-androgens (steroidal and non-steroidal), vascular disrupting agents, anti-angiogenic agents, anti-VEGFR agents, IL8 inhibitors, NO synthase inhibitors, vasoconstricting agents, vasodilating agents, and radiotherapeutic modalities.

29. The method according to claim 28 wherein the one or more additional cancer treatments is at least one anti-androgen.

30. The method according to claim 29 wherein the at least one anti-androgen is selected from the group consisting of flutamide, nilutamide, bicalutamide, finasteride, dutasteride, bexlosteride, izonsteride, turosteride, epristeride, abiraterone and combinations thereof.

31. The method according to claim 30 wherein the at least one anti-androgen is bicalutamide.

32. The method according to claim 27 wherein the one or more additional cancer treatments decreases tumour oxygenation in vivo.

33. The method according to claim 32 wherein the one or more additional cancer treatments lowers the median oxygen level of the tumour to below 3%.

34. A method of detecting hypoxic cells in vitro or in vivo in a group of cells, the method comprising:
exposing a compound of Formula VI:

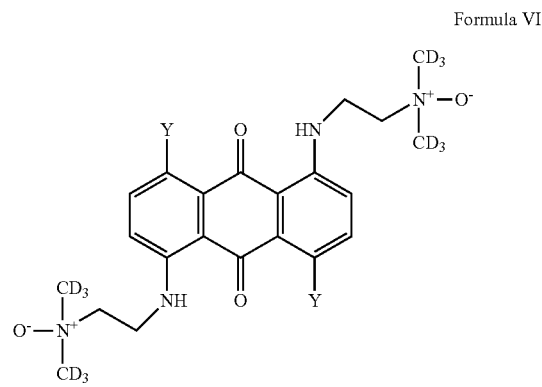

Formula VI wherein Y are each independently selected from the group consisting of hydrogen, hydroxy, halogeno, amino, $C_{1-4}$ alkoxy and $C_{2-8}$ alkanoxy
to the group of cells;
analysing the cells for the presence of a corresponding reduced compound of Formula IV Formula IV and determining the hypoxic cells based on the presence of the corresponding reduced compound.

35. The method according to claim 34 wherein the cells are mammalian.

36. The method according to claim 34 in vitro.

37. The method according to claim 34 in vivo.

38. The method according to claim 37, further comprising:
surgically excising cells identified as being hypoxic.

39. The method according to claim 34 wherein the compound is used in combination with a non-deuterated form of a compound of Formula VI.

40. The method according to claim 34 wherein the compound is detected using a method selected from the group consisting of mass spectrometry, nuclear magnetic resonance, infrared spectroscopy, colorimetrically, Raman spectroscopy, nuclear magnetic resonance, affinity capture methods, immunohistochemistry, flow cytometry, microscopy and antibody-based detection methods.

41. The method according to claim 35, wherein the cells are human.

* * * * *